(12) United States Patent
Gilbert et al.

(10) Patent No.: US 8,725,423 B2
(45) Date of Patent: May 13, 2014

(54) REPLICATION TIMING PROFILES FOR LEUKEMIA AND OTHER CANCERS

(71) Applicants: David M. Gilbert, Tallahassee, FL (US); Tyrone Ryba, Tallahassee, FL (US)

(72) Inventors: David M. Gilbert, Tallahassee, FL (US); Tyrone Ryba, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 0 days.

(21) Appl. No.: 13/726,803

(22) Filed: Dec. 26, 2012

(65) Prior Publication Data

US 2013/0184998 A1 Jul. 18, 2013

Related U.S. Application Data

(60) Provisional application No. 61/580,401, filed on Dec. 27, 2011.

(51) Int. Cl.
G06F 19/26 (2011.01)
(52) U.S. Cl.
USPC .............................................. 702/19; 435/6.1
(58) Field of Classification Search
None
See application file for complete search history.

(56) References Cited

U.S. PATENT DOCUMENTS

2012/0322675 A1 12/2012 Gilbert et al.

OTHER PUBLICATIONS

Ryba, T., Battaglia, D., Chang, B.H., Shirley, J.W., Buckley, Q., Pope, B.D., Devidas, M., Druker, B.J., and Gilbert D.M. "Abnormal developmental control of replication-timing domains in pediatric acute lymphoblastic leukemia," Genome Res. 22(10):1833-44 (2012).
Acquafreda, T., Soprano, K. J., Soprano D. R. "GPRC5A: A potential tumor suppressor and oncogene" Cancer. Biol. Ther. 8: 963-65 (2009).
Adolph, S., Hameister, H., Schildkraut, C. L. "Molecular analysis of the aberrant banding pattern on chromosome 15 in murine T-cell lymphomas." Chromosoma 101: 388-98 (1992).
Amiel, A., Elis, A., Sherker, S., Gaber, E., Manor, Y., Fejgin, M. D. "The influence of cytogenetic aberrations on gene replication in chronic lymphocytic leukemia patients." Cancer Genet. Cytogenet. 125: 81-86 (2001).
Amiel, A., Elis, A., Maimon, O., Ellis, M., Herishano, Y., Gaber, E., Fejgin, M. D., Lishner, M. "Replication status in leukocytes of treated and untreated patients with polycythemia vera and essential thrombocytosis." Cancer Genet. Cytogenet. 133: 34-38 (2002).
Bibikova, M., Chudin, E., Wu, B., Zhou, L., Garcia E. W., Liu, Y., Shin, S., Plaia, T. W., Auerbach, J. M., Arking, D. E., et al. "Human embryonic stem cells have a unique epigenetic signature." Genome Res 16: 1075-83 (2006).
Bienz, M., Ludwig, M., Leibundgut, E. O., Mueller, B. U., Ratschiller, D., Solenthaler, M., Fey, M. F., Pabst, T. "Risk assessment in patients with acutemyeloid leukemia and a normal karyotype." Clin. Cancer Res. 11: 1416-24 (2005).
Brauninger, A., Goossens, T., Rajewsky, K, Kuppers, R. "Regulation of immunoglobulin light chain gene rearrangements during early B cell development in the human." Eur. J. Immunol. 31: 3631-37 (2001).
Breger, K. S., Smith, L., Thayer. M. J. "Engineering translocations with delayed replication: Evidence for cis control of chromosome replication timing." Hum. Mol. Genet. 14: 2813-27 (2005).
Chang, B. H., Smith, L., Huang, J., Thayer, M. "Chromosomes with delayed replication timing lead to checkpoint activation, delayed recruitment of Aurora B and chromosome instability." Oncogene 26: 1852-61 (2007).
Chen, Y., Deng, J., Fujimoto, J., Kadara, H., Men, T., Lotan, D., Lotan, R. "Gprc5a deletion enhances the transformed phenotype in normal and malignant lung epithelial cells by eliciting persistent Stat3 signaling induced by autocrine leukemia inhibitory factor." Cancer Res. 70: 8917-26 (2010).
Collins-Underwood, J. R., Mullighan, C. G. "Genomic profiling of high-risk acute lymphoblastic leukemia." Leukemia 24: 1676-85 (2010).
Compte E, Pontarotti P, Collette Y, Lopez M, Olive D. 2004. Frontline: Characterization of BT3 molecules belonging to the B7 family expressed on immune cells. Eur. J. Immunol. 34: 2089-99 (2004).
Coolen, M. W., Stirzaker, C., Song, J. Z., Statham, A. L., Kassir, Z., Moreno C. S., Young, A. N., Varma, V., Speed, T. P., Cowley, M., et al. "Consolidation of the cancer genome into domains of repressive chromatin by long-range epigenetic silencing (LRES) reduces transcriptional plasticity." Nat. Cell. Biol. 12: 235-46 (2010).
De. S., Michor, F. "DNA replication timing and long-range DNA interactions predict mutational landscapes of cancer genomes." Nat. Biotechnol. 29: 1103-08 (2011).
Eul, J., Gronemeyer, H., Adolph, S., Hameister, H. "Suppression of tumorigenicity in T-cell lymphoma hybrids is correlatedwith changes in myc expression and DNA replication of the myc chromosomal domain." Chromosoma 96: 248-54 (1988).
Ferrando, A. A., Neuberg, D. S., Staunton, J., Loh, M. L., Huard, C., Raimondi, S. C., Behm, F. G., Pui, C. H., Downing, J. R., Gilliland, D. G., et al. "Gene expression signatures define novel oncogenic pathways in T cell acute lymphoblastic leukemia." Cancer Cell 1: 75-87 (2002).
Gilbert, D.M. "Evaluating genome-scale approaches to eukaryotic DNA replication." Nat. Rev. Genet. 11: 673-84 (2010).
Hansen, K. D., Timp, W., Bravo, H. C., Sabunciyan, S., Langmead, B., McDonald, O. G., Wen, B., Wu, H., Liu, Y., Diep, D., et al. "Increased methylation variation in epigenetic domains across cancer types." Nat. Genet. 43: 768-75 (2011).
Hiraoka, N., Nakagawa, H., Ong, E., Akama, T. O., Fukuda, M. N., Fukuda, M. "Molecular cloning and expression of two distinct human chondroitin 4-O-sulfotransferases that belong to the HNK-1 sulfotransferase gene family." J. Biol. Chem. 275: 20188-96 (2000).

(Continued)

*Primary Examiner* — Tracy Vivlemore
*Assistant Examiner* — Karen S Weiler
(74) *Attorney, Agent, or Firm* — Alchemy-Partners, PC

(57) ABSTRACT

Described is a method for determining that a population of cells are a specific type of leukemic cell based on the replication timing fingerprint for the population of cells.

7 Claims, 16 Drawing Sheets

(56) References Cited

OTHER PUBLICATIONS

Hiratani, I., Ryba, T., Itoh, M., Yokochi, T., Schwaiger, M., Chang, C. W., Lyou, Y., Townes, T. M., Schubeler, D., Gilbert, D. M. "Global reorganization of replication domains during embryonic stem cell differentiation." PLoS Biol. 6: e245. doi: 10.1371/journal.pbio. 0060245 (2008).

Hiratani, I., Takebayashi, S., Lu, J., Gilbert, D. M. "Replication timing and transcriptional control: Beyond cause and effect—part II." Curr. Opin. Genet. Dev. 19: 142-49 (2009).

Hiratani, I., Ryba, T., Itoh, M., Rathjen, J., Kulik, M., Papp, B., Fussner, E., Bazett-Jones, D. P., Plath, K., Dalton, S., et al. "Genome-wide dynamics of replication timing revealed by in vitro models of mouse embryogenesis." Genome Res. 20: 155-69 (2010).

Horsley, S. W., MacKay, A., Iravani, M., Fenwick, K., Valgeirsson, H., Dexter, T., Ashworth, A., Kearney, L. "Array CGH of fusion gene-positive leukemia-derived cell lines reveals cryptic regions of genomic gain and loss." Genes Chromosomes Cancer 45: 554-64 (2006).

Hsu, P. Y., Hsu, H. K., Singer, G. A., Yan, P. S., Rodriguez, B. A., Liu, J. C., Weng, Y. I., Deatherage, D. E., Chen, Z., Pereira, J. S., et al. Estrogen-mediated epigenetic repression of large chromosomal regions through DNA looping. Genome Res. 20: 733-44 (2010).

Hunger, S. P., Fall, M. Z., Camilla, B. M., Carroll, A. J., Link, M. P., Lauer, S. J., Mahoney, D. H., Pullen, D. J., Shuster, J. J., Steuber, C. P., et al. "E2A-PBX1 chimeric transcript status at end of consolidation is not predictive of treatment outcome in childhood acute lymphoblastic leukemias with a t(1;19)(q23;p13): A Pediatric Oncology Group study." Blood 91: 1021-28 (1998).

Jeha, S., Pui, C. H. "Risk-adapted treatment of pediatric acute lymphoblastic leukemia." Hematol. Oncol. Clin. North Am. 23: 973-90 (2009).

Kearney, L., Horsley, S. W. "Molecular cytogenetics in haematological malignancy: current technology and future prospects." Chromosoma 114: 286-94 (2005).

Korenstein-Ilan, A., Amiel, A., Lalezari, S., Lishner, M., Avivi, L. "Allele-specific replication associated with aneuploidy in blood cells of patients with hematologic malignancies." Cancer Genet. Cytogenet. 139: 97-103 (2002).

Lieberman-Aiden, E, van Berkum, N. L., Williams, L., Imakaev, M., Ragoczy, T., Telling, A., Amit, I., Lajoie, B. R., Sabo, P. J., Dorschner, M. O., et al. "Comprehensive mapping of long-range interactions reveals folding principles of the human genome." Science 326: 289-93 (2009).

Liu, P., Erez, A., Nagamani, S. C., Dhar, S. U., Kolodziejska, K. E., Dharmadhikari, A. V., Cooper, M. L., Wiszniewska, J., Zhang, F., Withers, M. A., et al. "Chromosome catastrophes involve replication mechanisms generating complex genomic rearrangements." Cell 146: 889-903 (2011).

Luo, X. Q., Ke, Z. Y., Huang, L. B., Guan, X. Q., Zhang, Y. C., Zhang, X. L. "High-risk childhood acute lymphoblastic leukemia in China: Factors influencing the treatment and outcome." Pediatr. Blood Cancer 52: 191-95 (2009).

Marcucci, G., Baldus, C. D., Ruppert, A. S., Radmacher, M. D., Mrozek, K., Whitman, S. P., Kolitz, J., Edwards, C. G., Vardiman, J. W., Powell, B. L., et al. "Overexpression of the ETS-related gene, ERG, predicts a worse outcome in acute myeloid leukemia with normal karyotype: A cancer and leukemia group B study." J. Clin. Oncol. 23: 9234-42 (2005).

Mathas, S., Kreher, S., Meaburn, K. J., Johrens, K., Lamprecht, B., Assaf, C., Sterry, W., Kadin, M. E., Daibata, M., Joos, S., et al. "Gene deregulation and spatial genome reorganization near breakpoints prior to formation of translocations in anaplastic large cell lymphoma." Proc. Natl. Acad. Sci. 106: 5831-36 (2009).

McKenna, R. W., Washington, L. T., Aquino, D. B., Picker, L. J., Kroft, S. H. "Immunophenotypic analysis of hematogones (B-lymphocyte precursors) in 662 consecutive bone marrow specimens by 4-color flow cytometry." Blood 98: 2498-2507 (2001).

Mulligahn, C. G., Goorha, S., Radtke, I., Miller, C. B., Coustan-Smith, E., Dalton, J. D., Girtman, K., Mathew, S., Ma, J., Pounds, S. B., et al. "Genome-wide analysis of genetic alterations in acute lymphoblastic leukaemia." Nature 446: 758-764, published Apr. 12, 2007.

Nemazee, D. "Receptor editing in lymphocyte development and central tolerance." Nat. Rev. Immunol. 6: 728-40 (2006).

Niebuhr, B., Fischer, M., Tager, M., Cammenga, J., Stocking, C. "Gatekeeper function of the RUNX1 transcription factor in acute leukemia." Blood Cells Mol. Dis. 40: 211-18 (2008).

Okuda, T., Mita, S., Yamauchi, S., Matsubara, T., Yagi, F., Yamamori, D., Fukuta, M., Kuroiwa, A., Matsuda, Y., Habuchi, O. "Molecular cloning, expression, and chromosomal mapping of human chondroitin 4-sulfotransferase, whose expression pattern in human tissues is different from that of chondroitin 6-sulfotransferase." J. Biochem. 128: 763-70 (2000).

Pope, B. D., Tsumagari, K., Battaglia, D., Ryba, T., Hiratani, I., Ehrlich, M., Gilbert, D. M. "DNA replication timing is maintained genome-wide in primary human myoblasts independent of D4Z4 contraction in FSH muscular dystrophy." PLoS ONE 6: e27413. doi: 10.1371/journal.pone.0027413 (2011).

Pui, C. H., Carroll, W. L., Meshinchi, S., Arceci, R. J. "Biology, risk stratification, and therapy of pediatric acute leukemias: An update." J. Clin. Oncol. 29: 551-65 (2011).

Pujadas, E., Feinberg, A. P. "Regulated noise in the epigenetic landscape of development and disease." Cell 148: 1123-31 (2012).

Rhodes, D. A., Stammers, M., Malcherek, G., Beck, S., Trowsdale, J. "The cluster of BTN genes in the extended major histocompatibility complex." Genomics 71: 351-62 (2001).

Ryba, T., Hiratani, I., Lu, J., Itoh, M., Kulik, M., Zhang, J., Schulz, T. C., Robins, A. J., Dalton, S., Gilbert, D. M. "Evolutionarily conserved replication timing profiles predict long-range chromatin interactions and distinguish closely related cell types." Genome Res. 20: 761-70 (2010).

Ryba, T., Battaglia, D., Pope, B. D., Hiratani, I., Gilbert, D. M. "Genome-scale analysis of replication timing: From bench to bioinformatics." Nat. Protoc. 6: 870-95 (2011a).

Ryba, T., Hiratani, I., Sasaki, T., Battaglia, D, Kulik, M., Zhang, J., Dalton, S., Gilbert, D. M. "Replication timing: A fingerprint for cell identity and pluripotency." PloS Comput. Biol. 7: e1002225. doi: 10.1371/journal.pcbi.1002225 (2011b).

Schlesinger, S., Selig, S., Bergman, Y., Cedar, H. "Allelic inactivation of rDNA loci." Genes Dev. 23: 2437-47 (2009).

Schmidt, H. H., Dyomin, V. G., Palanisamy, N., Itoyama, T., Nanjangud, G., Pirc-Danoewinata, H., Haas, O. A., Chaganti, R. S. "Deregulation of the carbohydrate (chondroitin 4) sulfotransferase 11 (CHST11) gene in a B-cell chronic lymphocytic leukemia with a t(12;14)(q23;q32)." Oncogene 23: 6991-96 (2004).

Smith, L., Plug, A., Thayer, M. "Delayed replication timing leads to delayed mitotic chromosome condensation and chromosomal instability of chromosome translocations." Proc. Natl. Acad. Sci. 98: 13300-05 (2001).

Smith, I. A., Knezevic, B. R., Ammann, J. U., Rhodes, D. A., Aw, D., Palmer, D. B., Mather, I. H., Trowsdale, J. "BTN1A1, the mammary gland butyrophilin, and BTN2A2 are both inhibitors of T cell activation." J. Immunol. 184: 3514-25 (2010).

Strefford, J. C., An, Q., Harrison, C. J. "Modeling the molecular consequences of unbalanced translocations in cancer: Lessons from acute lymphoblastic leukemia." Cell Cycle 8: 2175-84 (2009).

Sun, Y., Wyatt, R. T., Bigley, A., Krontiris, T. G. "Expression and replication timing patterns of wildtype and translocated BCL2 genes." Genomics 73: 161-70 (2001).

Tang, J. Q., Bene, M. C., Faure, G. C. "Alternative rearrangements of immunoglobulin light chain genes in human leukemia." Leukemia 5: 651-656 (1991), Abstract only.

Tao, Q., Fujimoto, J., Men, T., Ye, X., Deng, J., Lacroix, L., Clifford, J. L., Mao, L., Van Pelt, C. S., Lee. J. J., et al. "Identification of the retinoic acid-inducible Gprc5a as a new lung tumor suppressor gene." J. Natl. Cancer. Inst. 99: 1668-82 (2007).

Usvasalo, A., Raty, R., Harila-Saari, A., Koistinen, P., Savolainen, E. R., Vettenranta, K, Knuutila, S., Elonen, E., Saarinen-Pihkala, U. M. "Acute lymphoblastic leukemias with normal karyotypes are not without genomic aberrations." Cancer Genet. Cytogenet. 192: 10-17 (2009).

(56) References Cited

OTHER PUBLICATIONS

Weddington, N., Stuy, A, Hiratani, I., Ryba, T., Yokochi, T., Gilbert, D. M., "Replication Domain: A visualization tool and comparative database for genome-wide replication timing data." BMC Bioinformatics 9: 530. doi:10.1186/1471-2105-9-330 (2008).

Wiemels, J. L., Alexander, F. E., Cazzaniga, G., Biondi, A., Mayer, S. P., Greaves, M., "Microclustering of TEL-AML1 translocation breakpoints in childhood acute lymphoblastic leukemia." Genes Chromosomes Cancer 29: 219-28 (2000).

Xu, J., Sankaran, V. G., Ni, M., Menne, T. F., Puram, R. V., Kim, W., Orkin S. H. "Transcriptional silencing of g-globin by BCL11A involves long-range interactions and cooperation with SOX6." Genes Dev. 24: 783-98 (2010).

Yeoh, E. J., Ross, M. E., Shurtleff, S. A., Williams, W. K., Patel, D., Mahfouz, R., Behm, F. G., Raimondi, S. C., Relling, M. V., Patel, A., et al. "Classification, subtype discovery, and prediction of outcome in pediatric acute lymphoblastic leukemia by gene expression profiling." Cancer Cell 1: 133-43 (2002).

Percent change from B-lymphoblasts

| | | EtoL | LtoE |
|---|---|---|---|
| | T-lymphoblast | 0.5% | 4.3% |
| B-lymphoblasts | C0202.R1 | 0.6% | 0.0% |
| | C0202.R2 | 0.3% | 0.0% |
| | GM06990.R1 | 0.0% | 0.0% |
| | GM06990.R2 | 0.0% | 0.0% |
| | GM06999.R1 | 0.0% | 0.0% |
| | GM06999.R2 | 0.0% | 0.0% |
| | NC.NC.R1 | 0.1% | 0.8% |
| | NC.NC.R2 | 0.0% | 0.3% |
| Patient samples | 11.064.R1 | 2.6% | 13.0% |
| | 11.064.R2 | 2.4% | 13.2% |
| | 11.118.R1 | 5.4% | 8.1% |
| | 11.118.R2 | 5.5% | 9.0% |
| | 11.132.R1 | 1.6% | 7.2% |
| | 11.132.R2 | 1.7% | 7.1% |
| | 10-822.R1 | 8.8% | 2.5% |
| | 10-822.R2 | 10.9% | 2.6% |
| | 10-822.R3 | 9.2% | 2.5% |

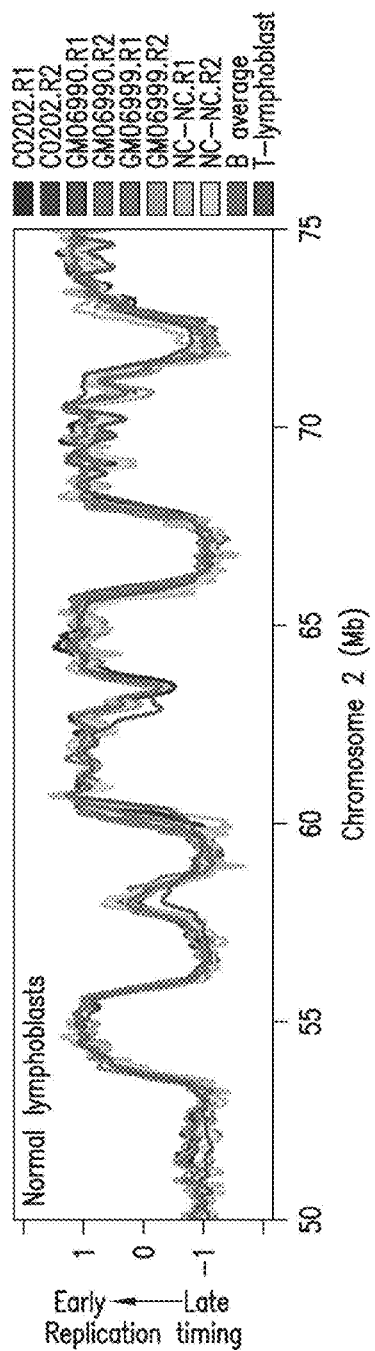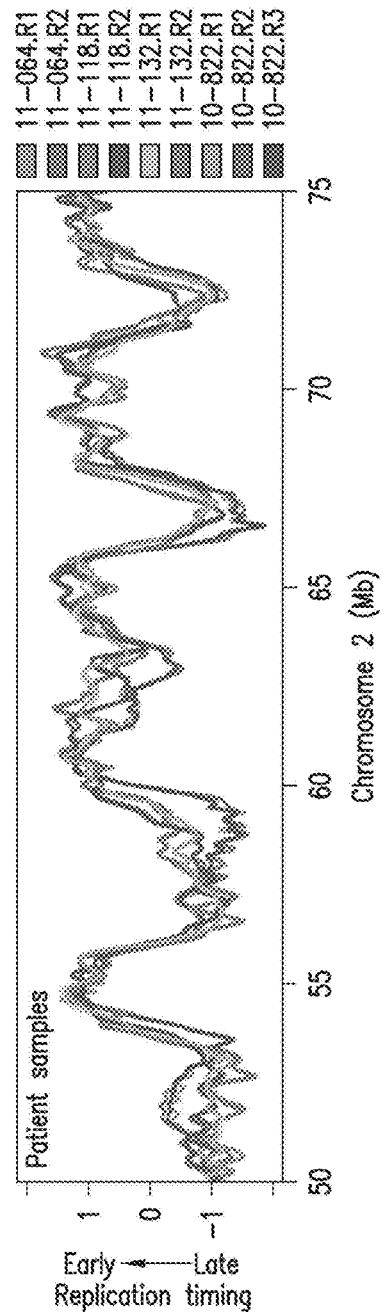

| Replication Pattern | REH | GM06990 |
|---|---|---|
| Probe 1 – Singlet<br>Probe 2 – Doublet | 9.6% | 16.9% |
| Probe 1 – Doublet<br>Probe 2 – Singlet | 35.1% | 12.1% |

| Replication Pattern | REH | GM06990 |
|---|---|---|
| Probe 1 – Doublet<br>Probe 2 – Single | 16.6% | 5.5% |
| Probe 1 – Singlet<br>Probe 2 – Doublet | 11.0% | 46.0% |

| | Developmental Change | | Not developmental but respects a boundary | | |
|---|---|---|---|---|---|
| | Yes | No | Yes | No | Cannot determine |
| Pan-leukemic | 13 | 2 | 2 | 0 | 0 |
| Class-specific | 6 | 16 | 15 | 0 | 1 |
| Sample-specific | 13 | 13 | 7 | 0 | 6 |
| Total | 32 | 31 | 24 | 0 | 7 |
| %Total | 50.8% | 49.2% | 100% (All either respect developmental boundaries or have constitutive timing) | | |

REPLICATION TIMING PROFILES FOR LEUKEMIA AND OTHER CANCERS

GOVERNMENT INTEREST STATEMENT

The United States Government may have rights in this invention pursuant to National Institutes of Health (NIH) Grant No. R21CA161666-01A1.

CROSS-REFERENCE TO RELATED APPLICATIONS

This application claims benefit of priority to U.S. Provisional Patent Application No. 61/580,401 to Gilbert et al., entitled "REPLICATION TIMING PROFILES FOR LEUKEMIA AND OTHER CANCERS," filed Dec. 27, 2011 which is incorporated by reference in its entirety.

BACKGROUND

1. Field of the Invention

The present invention relates to the use of replication timing profiles.

2. Related Art

Current biomarkers for cancer involve various types of test such as tests for chromosome abnormalities (karyotype abnormalities such as chromosome number differences or translocations) and gene expression tests. But these biomarkers are only partially effective at diagnosis.

SUMMARY

According to a first broad aspect, the present invention provides a method comprising the following steps: (a) determining that a population of cells are a specific type of leukemic cell based on the replication timing fingerprint for the population of cells; and (b) displaying to a user on a visual display device the type of leukemia determined step (a); wherein step (a) is conducted by a computer.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 2 shows loess-smoothed replication profiles for an exemplary 25-Mb chromosomal segment.

FIG. 4 shows profiles of four arbitrary patient samples, which diverge from each other and from lymphoblastoid B cells in a chromosome that did not harbor karyotypic rearrangements.

FIG. 5 shows a dendrogram expressing relatedness between the various cell samples and a chart showing the genome-wide correlations between control and leukemic lymphoblasts and cell types and FIG. 5-1 is a continuation of the dendrogram of FIG. 5.

DETAILED DESCRIPTION OF THE PREFERRED EMBODIMENTS

Definitions

Figures 1, 3:
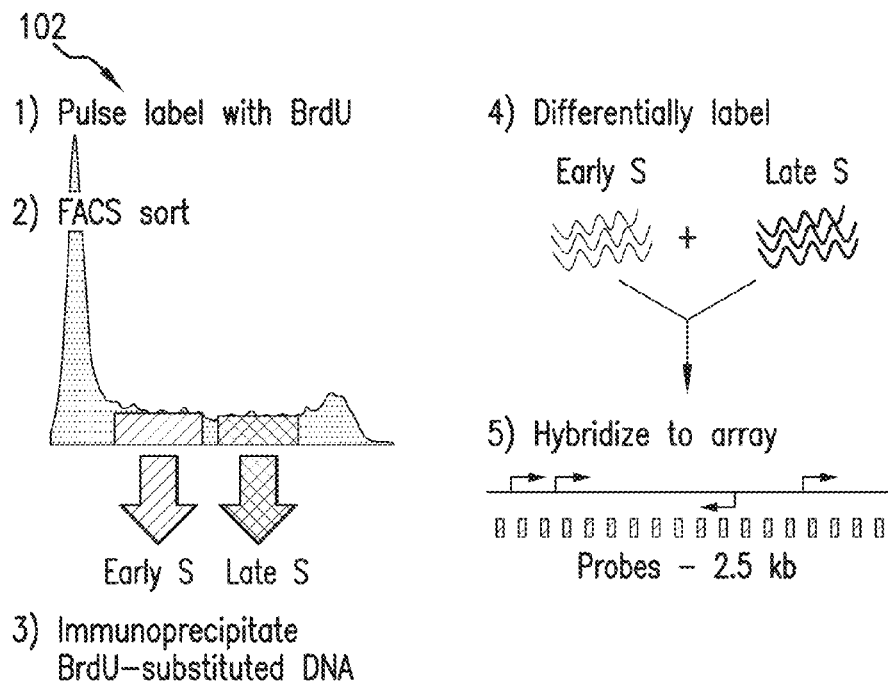
FIG. 1 is a diagram illustrating a protocol for generating genome-wide replication-timing profiles.
FIG. 3 shows a table summarizing the percentage of the genome with significant timing changes between biological replicates of the four lymphoblastoid cell lines.

Where the definition of terms departs from the commonly used meaning of the term, applicant intends to utilize the definitions provided below, unless specifically indicated.

For purposes of the present invention, it should be noted that the singular forms, "a," "an" and "the," include reference to the plural unless the context as herein presented clearly indicates otherwise.

For purposes of the present invention, a value or property is "based" on or "derived" from a particular value, property, the satisfaction of a condition or other factor if that value is derived by performing a mathematical calculation or logical decision using that value, property, condition or other factor.

For purposes of the present invention, the term "array" and the term "microarray," when used to determine the replication timing profile for a population of cells, refer interchangeably to a field or array of a multitude of spots corresponding to nucleic acid probes or oligonucleotides for all or at least a portion of the genome of a species placed on a support or substrate to allow for simultaneous detection and/or quantification of nucleic acid molecules present in one or more sample(s) by hybridization as commonly understood in the art. For purposes of the present invention, the term "array" generally refers to a genomic array, such as a comparative genomic hybridization (CGH) array, a tiling array, etc.

For purposes of the present invention, the term "cell type" refers to the kind, identity and/or classification of cells according to any and all criteria, such as their tissue and species of origin, their differentiation state, whether or not (and in what manner) they are normal or diseased, etc. For example, the term "cell type" may refer separately and specifically to any specific kind of cell found in nature, such as an embryonic stem cell, a neural precursor cell, a myoblast, a mesodermal cell, etc. Such a list of possible cell types is meant herein to be unlimited.

For purposes of the present invention, the term "computer" refers to any type of computer or other device that implements software, including an individual computer such as a personal computer, laptop computer, tablet computer, mainframe computer, mini-computer, etc. A computer also refers to electronic devices such as a smartphone, an eBook reader, a cell phone, a television, a handheld electronic game console, a video game console, a compressed audio or video player such as an MP3 player, a Blu-ray player, a DVD player, a microwave oven, etc. In addition, the term "computer" refers to any type of network of computers, such as a network of computers in a business, a computer bank, the Cloud, the Internet, etc. A computer may include a storage device, memory or other hardware and/or software for loading computer programs or other instructions into the computer. A computer may include a communication unit. The communication unit may allow the computer to connect to other databases and the Internet through an I/O interface. The communication unit may allow the transfer to, as well as reception of data from, other databases. The communication unit may include a modem, an Ethernet card or any similar device that enables the computer system to connect to databases and networks such as LAN, MAN, WAN and the Internet. A computer may facilitate inputs from a user through an input device, accessible to the system through an I/O interface. A computer may execute a set of instructions that are stored in one or more storage devices, in order to process input data. The storage devices may also hold data or other information as desired. The storage element may be in the form of an information source or a physical memory element present in the processing machine. The set of instructions may include various commands that instruct the processing machine to perform specific tasks, such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing or a request made by another processing machine. In one embodiment of the present invention a computer may be used to implement steps of the method of the present invention and steps of the various protocols described below.

For purposes of the present invention, the term "differential," the term "replication timing profile differential" and the term "replication timing differential" refer interchangeably to differences in replication timing values between any combination of: (1) one or more replication timing profile(s); (2) a replication timing fingerprint; and/or (3) one or more informative segment(s) of a replication timing fingerprint. For example, the "replication timing differential" may refer to differences in replication timing ratios, such as differences in replication timing ratios expressed on a logarithmic scale, between two or more populations of cells or cell types at a given genomic or chromosomal locus or along the length of at least a segment of one or more chromosome(s) within a genome, etc.

For purposes of the present invention, the term "epigenetic signature" and the term "epigenetic signatures" broadly refer to any manifestation or phenotype of cells of a particular cell type that is believed to derive from the chromatin structure of such cells.

For purposes of the present invention, the term "epigenetics," the term "epigenetic markers" and the term "epigenetic parameters" generally refer to chemical modifications of DNA, histones or other chromatin-associated molecules that impart changes in gene expression, such as methylation, acetylation, ubiquitylation, etc. However, the terms "epigenetics," "epigenetic markers" and "epigenetic parameters" may refer more generally to any changes in chromatin structure that affect gene expression apart from DNA sequence. For example, the terms "epigenetics," "epigenetic markers" and "epigenetic parameters" may refer to incorporation of histone variants or chromosomal remodeling by enzymes.

For purposes of the present invention, the term "genome-wide" and the term "whole genome" may refer interchangeably to the entire genome of a cell or population of cells. Alternatively, the terms "genome-wide" or "whole genome" may refer to most or nearly all of the genome. For example, the terms "genome-wide" or "whole genome" may exclude a few portions of the genome that are difficult to sequence, do not differ among cells or cell types, are not represented on a whole genome array, or raise some other issue or difficulty that prompts exclusion of such portions of the genome.

For purposes of the present invention, the term "genomic array" is an array having probes and/or oligonucleotides corresponding to both coding and non-coding intergenic sequences for at least a portion of a genome and may include the whole genome of an organism. For example, a "genomic array" may have probes and/or oligonucleotides for only those portions of a genome of an organism that correspond to replication timing fingerprint(s) or informative segments of fingerprint(s). The term "genomic array" may also refer to a set of nucleic acid probes or oligonucleotides representing sequences that are about evenly spaced along the length of each chromosome or chromosomal segment. However, even spacing of probes may be dispensable with very high-density genomic arrays (i.e., genomic arrays having an average probe spacing of much less than about 6 kb).

For purposes of the present invention, the term "hardware and/or software" refers to a device that may be implemented by digital software, digital hardware or a combination of both digital hardware and digital software.

For purposes of the present invention, the term "high resolution array" and the term "high resolution genomic array" generally refers a genomic array having sufficient resolution to provide enough information to generate a smooth replication timing profile to reliably determine the exact positions, lengths, boundaries, etc., of the replication timing domains. The term "high resolution array" or "high resolution genomic array" may correspond to the whole genome or a substantial portion of a genome of a particular cell or population of cells. The term "high resolution array" or "high resolution genomic array" may also refer to a genomic array having an average probe spacing of about 6 kilobases (kb) or less.

For purposes of the present invention, the term "informative segment" and the term "informative segments" refer to one or more contiguous portions or segments of one or more chromosome(s) within a genome that are used to define a replication timing fingerprint. In other words, the terms "informative segment" and "informative segments" may refer to one or more contiguous portions or segments of one or more chromosome(s) within a genome that differ between two or more different cell types. For example, the terms "informative segment" or "informative segments" may refer to one or more regions or segments of a genome for a population of cells of a particular cell type having the following characteristics: (1) the region covers at least about 50 kilobases (kb) of genomic DNA; and (2) the region has at least about a 0.5 replication timing ratio differential across such length compared to all other cell types, or at least compared to all other relevant cell types.

For purposes of the present invention, the term "machine-readable medium" refers to any mechanism that stores information in a form accessible by a machine such as a computer, network device, personal digital assistant, manufacturing tool, any device with a set of one or more processors, etc. For example, a machine-readable medium may be a recordable/non-recordable medium (e.g., a read-only memory (ROM), a random access memory (RAM), a magnetic disk storage medium, an optical storage medium, a flash memory device, etc.), a bar code, an RFID tag, etc.

For purposes of the present invention, the term "mammalian cells" refers to a population of cells that are, or were, originally derived from a mammalian organism. The term "mammalian cells" may include primary cells derived from a mammalian species or a cell line originally derived from a mammalian species. The term "mammalian cells" may refer to a homogeneous population of cells from a mammalian organism.

For purposes of the present invention, the term "population of cells" refers to a homogeneous group or population of cells. The term "population of cells" may also include a single cell in culture having the potential to grow and divide into a plurality of homogeneous cells under appropriate culturing conditions.

For purposes of the present invention, the term "primary cell" refers to a cell or cells isolated from a tissue of an organism and placed in culture. The "primary cell" may be derived from any tissue of any organism, such as a mammalian organism. The term "primary cell" generally includes any cell or cells that may be isolated from a tissue of an organism to create a reasonably homogeneous population of cells, such as by first creating single-cell suspensions.

For purposes of the present invention, the term "replication timing ratio" refers to a ratio value for the timing of replication at a particular locus of a chromosome within the genome of a cell. For example, the "replication timing ratio" may be a ratio of the extent of replication in early S-phase cells divided by the extent of replication in late S-phase cells, or vice versa, at a given locus. Alternatively, the replication timing ratio may be expressed on a logarithmic scale, such as log 2(early/late) or log 2(late/early). Alternatively, for example, the term "replication timing ratio" may refer to the ratio of the extent of replicated DNA in S-phase cells to the amount of DNA in G1-phase cells. The extent of replication or the amount of DNA may be measured, for example, by the fluorescence intensity of an attached label.

For purposes of the present invention, the term "replication timing domain" refers to a contiguous region of a chromosome of a cell or population of cells having roughly the same (i.e., early vs. late) replication timing, such as a contiguous region of a chromosome of a cell or population of cells having roughly the same replication timing ratio value.

For purposes of the present invention, the term "replication timing profile" refers to a series of values for replication timing (e.g., early versus late S-phase replication timing) along the length of at least a segment of one or more chromosome(s) within a genome. For example, the "replication timing profile" may be expressed as a series of replication timing ratio values, such as early/late S-phase replication or late/early S-phase replication, along the length of at least a segment of one or more chromosome(s), which may further be expressed on a logarithmic scale. Alternatively, the "replication timing profile" may refer to a ratio of the amounts of S-phase DNA to G1-phase DNA from a population of asynchronously dividing cells along the length of at least a segment of one or more chromosome(s), which further may be expressed on a logarithmic scale, with a higher ratio indicating earlier replication and a lower ratio indicating later replication. The term "replication timing profile" may include a replication timing fingerprint for a particular cell type or a set of replication timing profiles for informative segments of a replication timing fingerprint for a particular cell type. The term "replication timing profile" further may include a replication timing profile differential between any combination of: (1) one or more replication timing profile(s); (2) a replication timing fingerprint; and/or (3) one or more informative segment(s) of a replication timing fingerprint(s). The "replication timing profile" may be determined, for example, by quantifying an amount of replicated DNA in a sample from a population of cells by measuring fluorescently labeled DNA, by sequencing, etc.

For purposes of the present invention, the term "replication timing test profile" refers to the replication timing profile for a population of cells of interest having an unknown or uncertain identity to the user of the embodiments of the methods of the present invention.

For purposes of the present invention, the term "replication timing reference profile" refers to a replication timing profile used as a basis for comparison to identify and/or distinguish a population of cells based on the population's replication timing test profile. Such "replication timing reference profile" may include a replication timing profile for a population of cells, an average replication timing profile for a group of related or identical cells or from replicate experiments, a replication timing fingerprint, one or more informative segment(s) of a replication timing fingerprint, etc., or any combination thereof Such a "replication timing reference profile" may be simultaneously or previously determined, may be contained in a database, etc.

For purposes of the present invention, the term "replication timing fingerprint" refers to one or more segments or portions of a replication timing profile for a particular type of cell(s) that differs from all other cell types or all other relevant cell types, which may be used to identify, distinguish, etc., cells of that type. The term "replication timing fingerprint" may refer to the collection of all informative segments of a genome of cells of a particular cell type defined as segments that display a replication timing profile that differs from the replication timing profiles of one or more other cell types. The term "replication timing fingerprint" may further include one or more informative segment(s) that have replication timing profiles that are shared by two or more cell types (i.e., the replication timing profiles are identical or similar) for purposes of comparing a population of cells to a limited set of candidate cell types that have a different replication timing profile for such informative segment(s). A "replication timing fingerprint" may generally exclude uninformative segments that are not consistent among cells of the same type or that do not differ among cells of different types.

For purposes of the present invention, the term "resolution," with reference to arrays, refers to how much resolution may be achieved along the length of one or more chromosomes. In general, the more probes and/or oligonucleotides along a given length of a chromosome, the greater or higher the resolution may be for such length of a chromosome, assuming roughly equal spacing. Therefore, the terms "density" and "probe density" for an array are directly related to the term "resolution," since a greater or higher probe density along a given length of a chromosome would generally result in greater or higher resolution for the same length of a chromosome. Conversely, the term "spacing" or "probe spacing" is inversely related to gene density and resolution for an array, since a lower or reduced spacing on average between probes and/or oligonucleotides on the array as a function of chromosomal position would generally result in greater or higher resolution or probe density. For example, an array having an average "probe spacing" of about 6 kb or less along a length of a chromosome would have a "probe density" or "resolution" of about 6 kb or higher for such length of chromosome.

For purposes of the present invention, the term "storage" and the term "storage medium" refer to any form of storage that may be used to store bits of information. Examples of storage include both volatile and non-volatile memories such as ERAM, flash memory, floppy disks, Zip™ disks, CD-ROM, CD-R, CD-RW, DVD, DVD-R, DVD+R, hard disks, optical disks, etc.

For purposes of the present invention, the term "type of leukemia" refers to any distinguishable type of leukemia. The types of leukemia can be grouped based on how quickly the disease develops and gets worse. For example, leukemia may be considered either chronic (which usually gets worse slowly) or acute (which usually gets worse quickly). In the case of chronic leukemia, early in the disease, the leukemia cells can still do some of the work of normal white blood cells. People may not have any symptoms at first. Doctors often find chronic leukemia during a routine checkup—before there are any symptoms. Slowly, chronic leukemia gets worse. As the number of leukemia cells in the blood increases, people get symptoms, such as swollen lymph nodes or infections. When symptoms do appear, they are usually mild at first and get worse gradually. In the case of acute leukemia, the leukemia cells can't do any of the work of normal white blood cells. The number of leukemia cells increases rapidly. Acute leukemia usually worsens quickly. The types of leukemia also can be grouped based on the type of white blood cell that is affected. Leukemia can start in lymphoid cells or myeloid cells. Leukemia that affects lymphoid cells is called lymphoid, lymphocytic, or lymphoblastic leukemia. Leukemia that affects myeloid cells is called myeloid, myelogenous, or myeloblastic leukemia. There are four common types of leukemia: (1) chronic lymphocytic leukemia (CLL), (2) chronic myeloid leukemia (CML), (3) acute lymphocytic (lymphoblastic) leukemia (ALL) and (4) acute myeloid leukemia (AML). CLL affects lymphoid cells and usually grows slowly. It accounts for more than 15,000 new cases of leukemia each year. Most often, people diagnosed with the disease are over age 55. It almost never affects children. CML affects myeloid cells and usually grows slowly at first. It accounts for nearly 5,000 new cases of leukemia each year. It mainly affects adults. ALL affects lymphoid cells and grows quickly. It accounts for more than 5,000 new cases of leukemia each year. ALL is the most common type of leukemia in young children. It also affects adults. AML affects myeloid cells and grows quickly. It accounts for more than 13,000 new cases of leukemia each year. It occurs in both adults and children.

For purposes of the present invention, the term "visual display device" or "visual display apparatus" includes any type of visual display device or apparatus such as a CRT monitor, an LCD screen, an LED screen, a projected display, a printer for printing out an image such as a picture and/or text, etc. A visual display device may be a part of another device such as a computer monitor, television, projector, cell phone, smartphone, laptop computer, tablet computer, hand-held music and/or video player, personal digital assistant (PDA), handheld game player, head-mounted display, a heads-up display (HUD), global positioning system (GPS) receiver, automotive navigation system, dashboard, watch, microwave oven, electronic organ, automated teller machine (ATM), etc. A visual display device may be used to display to a user images of the various images, plots, graphs, etc. described below and shown in the drawings. A printer may "display" an image, plot, graph, etc. to a user by printing out the image, plot, graph, Description Abnormal replication timing has been observed in cancer but no previous study has comprehensively evaluated this misregulation. Genome-wide replication-timing profiles have now been generated for pediatric leukemias from 17 patients and three cell lines, as well as normal B and T cells. Nonleukemic EBV-transformed lymphoblastoid cell lines displayed highly stable replication-timing profiles that were more similar to normal T cells than to leukemias. Leukemias were more similar to each other than to B and T cells but were considerably more heterogeneous than nonleukemic controls. Some differences were patient specific, while others were found in all leukemic samples, potentially representing early epigenetic events. Differences encompassed large segments of chromosomes and included genes implicated in other types of cancer. Remarkably, differences that distinguished leukemias aligned in register to the boundaries of developmentally regulated replication-timing domains that distinguish normal cell types. Most changes did not coincide with copy-number variation or translocations. However, many of the changes that were associated with translocations in some leukemias were also shared between all leukemic samples independent of the genetic lesion, suggesting that they precede and possibly predispose chromosomes to the translocation. Altogether, these results identify sites of abnormal developmental control of DNA replication in cancer that reveal the significance of replication-timing boundaries to chromosome structure and function and support the replication domain model of replication-timing regulation. They also open new avenues of investigation into the chromosomal basis of cancer and provide a potential novel source of epigenetic cancer biomarkers.

DNA replication in human cells proceeds according to a defined temporal order (Hiratani et al. 2009 (Reference 22)). Several studies have identified abnormal temporal control of replication in many cancers (Amiel et al. 2001, 2002 (References 3 and 4); Smith et al. 2001 (Reference 49); Sun et al. 2001 (Reference 52); Korenstein-Ilan et al. 2002 (Reference 29)). For example, specific chromosome translocations result in a chromosome-wide delay in replication timing (Breger et al. 2005 (Reference 8); Chang et al. 2007 (Reference 9)) that is found frequently in cancer cells (Smith et al. 2001 (Reference 49)). Some cancer-specific replication-timing changes appear to be epigenetic in that, similar to developmental changes, they are mitotically stable but do not involve detectable genetic lesions (Eul et al. 1988 (Reference 16); Adolph et al. 1992 (Reference 2)). A far-reaching aspect of epigenetic abnormalities is that they are potentially reversible. In fact, in a mouse lymphoma model showing aberrant replication timing, fusion of affected cells with normal mouse fibroblasts restored the normal pattern of replication timing and reversed the malignant phenotype (Eul et al. 1988 (Reference 16); Adolph et al. 1992 (Reference 2)). Despite these observations, there has not been a comprehensive study to evaluate the extent of replication-timing abnormalities in cancer.

Genome-wide replication-timing profiles have been generated for a wide collection of human and mouse cell lines and embryonic stem cell (ESC) differentiation intermediates, revealing developmentally regulated changes in replication timing that encompass at least half of the genome (ReplicationDomain.org). Developmentally regulated changes take place in units of 400-800 kb and are associated with changes in subnuclear 3D organization of the affected domains (Hiratani et al. 2008, 2010 (References 21 and 23)). This replication-timing program is a highly stable epigenetic characteristic of a given cell type that is indistinguishable between the same cell types from different individuals (Pope et al. 2011). This stability has allowed for the development of tools to unambiguously determine cellular identity using their specific "replication fingerprints" (Ryba et al. 2011b (Reference 46)). Intriguingly, replication-timing profiles correlate more strongly with genome-wide maps of the sites and frequencies of chromatin interactions (Hi-C) (Lieberman-Aiden et al. 2009 (Reference 30) than with any other chromosomal property identified to date (Ryba et al. 2010 (Reference 44)), indicating that replication domains reflect the structural architecture of chromosomes and support the model of replication-timing domains as structural and functional large-scale units (the replication domain model). In summary, replication-timing profiles are unique to specific cell types and define an unexplored level of chromosome domain organization with intriguing potential for epigenetic fingerprinting.

Just as specific cell types display unique replication-timing fingerprints, specific cancers may also be definable by their replication-timing fingerprints. Acute lymphoblastic leukemia (ALL) is an excellent model cancer to investigate this hypothesis due to the availability of relatively homogeneous cancer tissue from affected patients and several well-characterized genetic subtypes linked to prognosis. Current clinical risk stratification for pediatric ALL includes factors such as age, leukocyte count at time of diagnosis, and recurrent chromosomal abnormalities detected in malignant lymphoblasts (Yeoh et al. 2002 (Reference 59); Jeha and Pui 2009 (Reference 27); Luo et al. 2009 (Reference 32)). Chromosomal abnormalities with prognostic significance include aneuploidies, such as hypodiploidy (<44 chromosomes) and hyperdiploidy (with trisomies 4, 10, and 17), translocations, and deletions (Pui et al. 2011 (Reference 41)). However, only a minority of these abnormalities such as t(9;22) show a direct activation of an oncogene, and the underlying mechanisms of tumorigenesis for the majority of ALL subtypes remain elusive. Furthermore, ~20% of ALL and 50% of AML cases present with a normal karyotype (Bienz et al. 2005 (Reference 6); Kearney and Horsley 2005 (Reference 28); Usvasalo et al. 2009 (Reference 55); Collins-Underwood and Mullighan 2010 (Reference 11); Pui et al. 2011 (Reference 41)) but have widely varying clinical outcomes, underscoring the need for additional epigeneticmarkers. Here the replication program is queried genome-wide in 17 primary childhood leukemias and three ALL cell lines and report widespread instability, with some changes in common to all leukemias and others unique to specific patients. The differences that distinguish different cancers also align with the boundaries of normal developmentally regulated replication domains, supporting the replication domain model. In addition, the timing changes that distinguish cancers from normal cells do not resemble any particular tissue, extending a model derived from DNA methylation studies that cancers are characterized by widespread epigenetic instability (Hansen et al. 2011 (Reference 19); Pujadas and Feinberg 2012 (Reference 42)).

Results

Replication Timing is Conserved Between Diverse Nonleukemic Lymphoblasts

The majority of patients during this study presented with pre-B ALL. Hence, the stability of replication-timing profiles is first evaluated between nonleukemic human B cells. Since proliferating immature B cells derived directly from patients are not available (immature B cells [hematogones] make up <5% of cells from the bone marrow of normal individuals and must be stimulated to proliferate ex vivo) (McKenna et al. 2001 (Reference 35)), four established nonleukemic EBV-transformed mature human B lymphoblastoid cell lines were analyzed: C0202, NC-NC, GM06990, and GM06999. A protocol 102 for generating genome-wide replication-timing profiles is summarized in FIG. 1, and has been described in detail in Ryba et al. 2011a (Reference 45). FIG. 2 shows loess-smoothed replication profiles for an exemplary 25-Mb chromosomal segment, while FIG. 3 summarizes the percentage of the genome with significant timing changes between biological replicates of the four lymphoblastoid cell lines. The high degree of conservation between these lines demonstrates that their replication-timing profiles are a stable characteristic of mature human B cells, even when comparing established cell lines from different sources and histories (Supplemental FIG. 1 of Reference 60). This extends previous results demonstrating the robust stability of replication profiles between common cell types (Hiratani et al. 2008, 2010 (Reference 21 and 23); Ryba et al. 2010 (Reference 44); Pope et al. 2011 (Reference 40)). The average of all replicates from these four cell lines provides a single B-cell-derived replication-timing profile that will herein be called "control" in comparisons with leukemia profiles, with the given caveat that leukemic samples are arrested at various stages in lymphoblast development from immature to more mature pre-B stages (Ferrando et al. 2002 (Reference 17); Nemazee 2006 (Reference 37); Mullighan et al. 2007 (Reference 36)) as indicated by their immunophenotypes where available (Supplemental Table 1 of Reference 60). To derive an approximation of the extent to which different types of lymphoblasts vary in replication timing, and since two patients presented with T-cell ALL, a mature CD4+ peripheral T-cell sample from a normal individual were also profiled (FIGS. 2 and 3). These results revealed that replication timing in mature B and T cells differs by only 4.5% genome wide. FIGS. 1, 2, 3 and 4 illustrate that RT profiles are stable in nonleukemic lymphoblasts, but diverge in leukemic samples. FIG. 1 shows a method for generating genome-wide replication-timing profiles. Dividing cells are pulse labeled with BrdU and FACS sorted into early and late S-phase fractions, and nascent BrdU-substituted DNA is differentially labeled and hybridized on a tiling CGH microarray with even probe spacing. FIG. 2 shows overlaid replication-timing profiles of a segment of human chromosome 2 for four nonleukemic EBV transformed human B-cell lines: C0202, GM06990, GM06999, and NC-NC. Each cell line is represented by loess-smoothed curves of two high-quality biological replicates (denoted R1 and R2; see Methods). The red profile is the average of the four B-cell lines, and in blue is a corresponding primary T-cell line. As shown in FIG. 3, the percentage of the genome with significant (>1 RT unit) timing changes toward earlier (L to E) or later (E to L) replication from the average normal B-cell profile, for each of the individual replicate profiles in FIGS. 2 and 3. FIG. 4 shows profiles of four arbitrary patient samples, which diverge from each other and from lymphoblastoid B cells in a chromosome that did not harbor karyotypic rearrangements.

Heterogeneous Replication Timing in Leukemia Cells

FIG. 4 shows profiles from four exemplary pre-B ALL patient samples across the same segment of chromosome 2 as shown in FIG. 2. In contrast to control mature B-cell lines, these cells show numerous differences in replication timing, even more than seen between mature B and T cells, while replicates of each patient sample are virtually indistinguishable. Altogether, three B-ALL cell lines, and 13 B-ALL, two T-ALL, and one AML leukemic patient samples were profiled. The properties of all 20 leukemic and five normal samples are summarized in Supplemental FIG. 1 of Reference 60, and cell cycle analyses for all samples are shown in Supplemental FIG. 2 of Reference 60.

Figure 5:
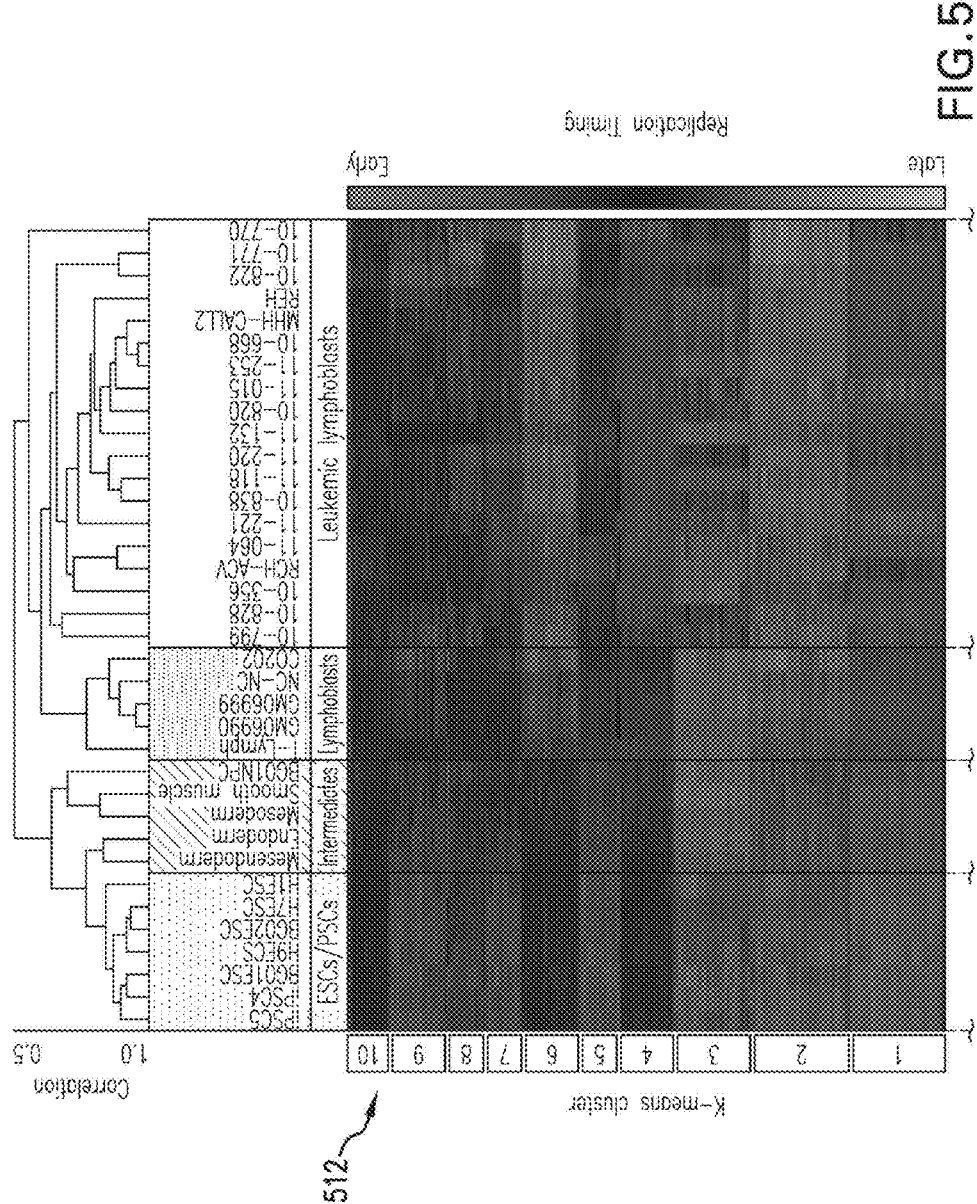
Figures 1, 5:
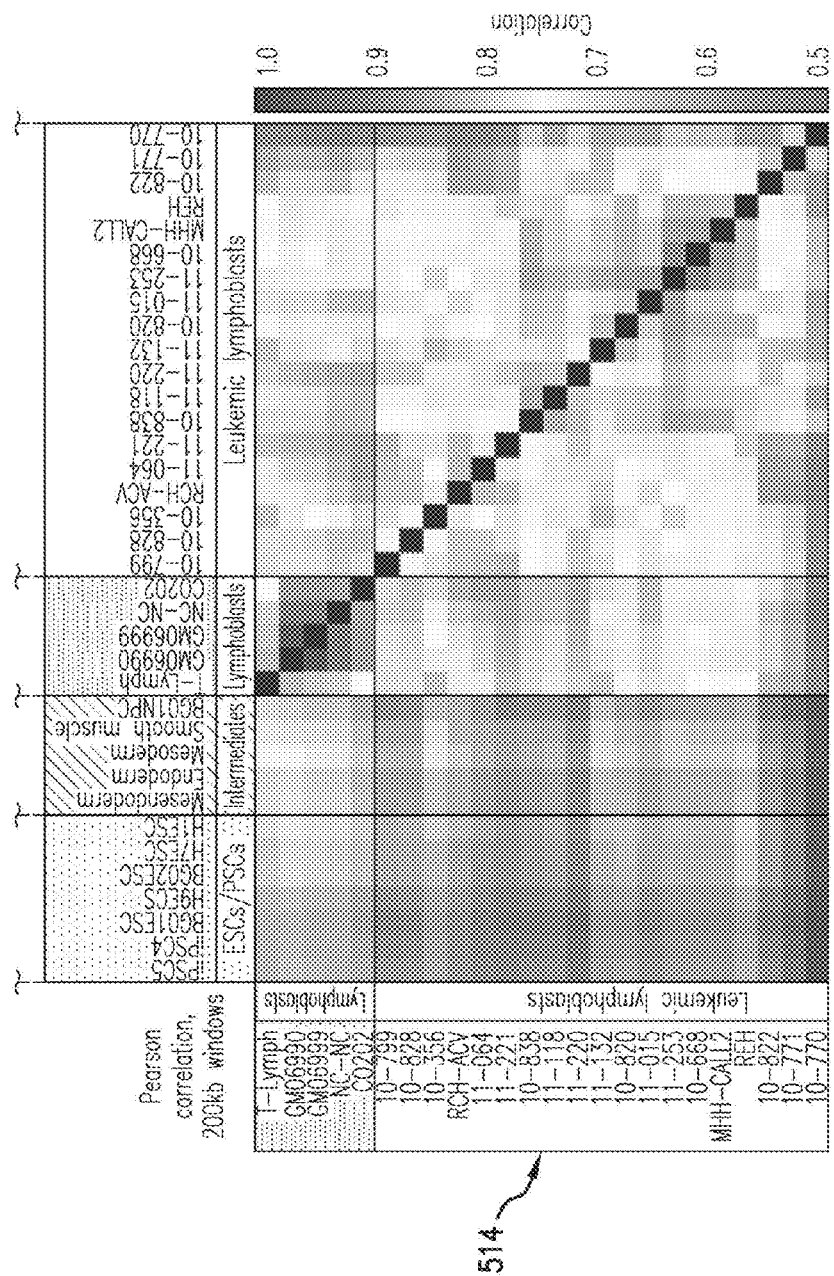

As an initial comparison, the genome was divided into 12,625 nonoverlapping 200-kb windows, and replication profiles were hierarchically clustered to create a dendrogram expressing relatedness between the various cell samples (dendogram 512 of FIG. 5). This, along with genome-wide correlations between control and leukemic lymphoblasts and cell types previously profiled (Chart 514 of FIG. 5) confirmed that replication profiles of individual leukemic samples were widely divergent and easily distinguished from control lymphoblasts, other human cell types, and each other. However, many differences from control cells were shared between leukemia samples despite their various stages of developmental arrest, suggesting that there are replication abnormalities in common between many types of leukemia. Control mature B- and T-cell profiles were distinct, but were more similar to each other than to leukemias of any origin. Nonetheless, T-ALL patient samples (10-828, 10-799) clustered separately from B-ALL, and samples with TCF3/PBX1 translocations (11-064, RCH-ACV) as well as those with mostly normal karyotypes (10-838, 11-118) formed their own clusters, suggesting conservation of features among developmentally related subgroups. Timing changes between leukemic and control cells occurred in a tight size distribution consistent with the 400-800-kb unit size of natural developmentally regulated changes in replication timing (FIG. 2C), and 9%-18% of domains detectably deviated from the controls in each leukemic cell line or patient sample (FIG. 2D), with consistent changes between replicates. With the notable exception of patient 10-822, most profiles had a significantly higher fraction of the genome replicating earlier than the controls (LtoE), rather than later (average 7.8% LtoE differences; 4.7% EtoL). The amount of change was generally not as great as the 20% of domains that differ between most cell types, but significantly higher than the 2%-4% of domains that deviate between cells of the same type, the 4.5% between B and T cells, or the 6.0% between human ESC-derived early endoderm vs. mesoderm tissues (FIGS. 1C, 2; Hiratani et al. 2010 (Reference 23); Ryba et al. 2010, 2011a (References 44 and 45)). Replication-timing changes were distributed throughout the genome on all chromosomes (Supplemental FIG. 3 of Reference 60) more evenly than the breakpoints present in patient samples, and unlike the phenomenon of chromothripsis, where multiple breaks are clustered on a single chromosome (Liu et al. 2011 (Reference 31)). All replication profiles reported here are freely available to view or download (Weddington et al. 2008 (Reference 56)).

Figure 7:
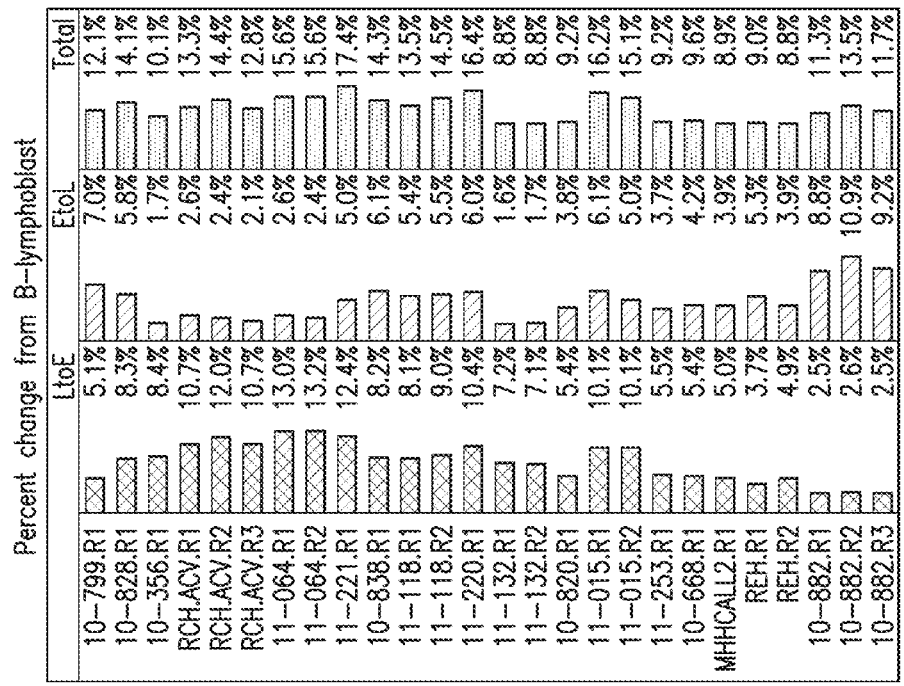
FIG. 7 shows the percentage of the genome with significant timing changes toward earlier (L to E) or later (E to L) replication from the normal B-cell profiles in indicated cell types.
Figure 6:
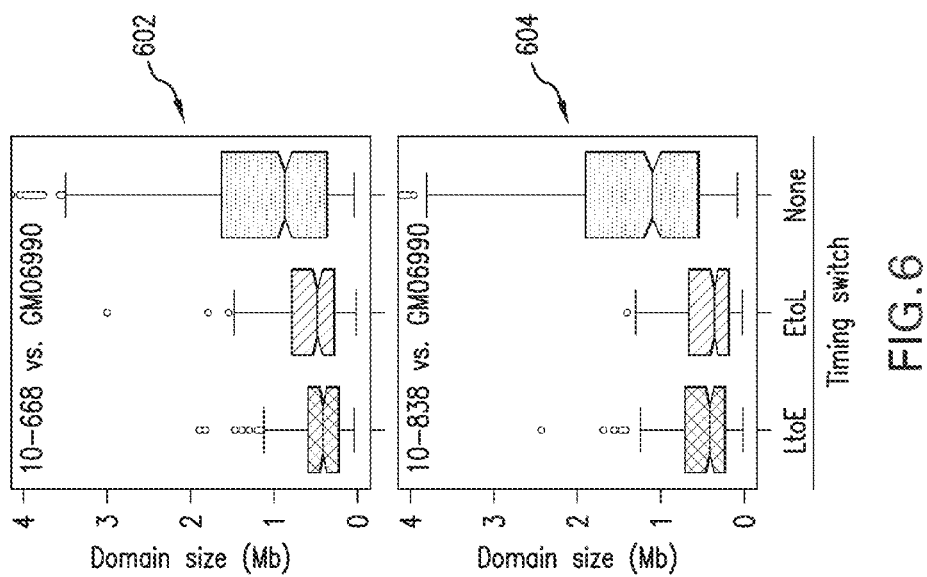
FIG. 6 shows two plots illustrating that domain-wide switches to earlier (L to E) replication timing or later (E to L) replication timing occur in units of 400-800 kb.

FIGS. 5, 5-1, 6 and 7 illustrate how leukemic cells show global changes in replication profiles. Chart 512 of FIGS. 5 and 5-1 shows the hierarchical clustering of genome-wide replication-timing patterns for the four lymphoblastoid B-cell lines and those of other human cell types, showing relatively stable profiles between mature B and T lymphoblasts, and clustering of samples with similar genetic makeup, including T-cell leukemias (10-799/10-828), those with TCF3/PBX1 translocations (11-064/RCH-ACV), and those with mostly normal karyotype (10-838/11-118). Chart 514 of FIGS. 5 and 5-1 shows genome-wide correlations between replication-timing data sets used in this study. Correlations between divergent B cells are consistently above 0.9, while those between leukemic samples generally range from 0.60 to 0.85. FIG. 6 shows domain-wide switches to earlier (L to E) replication timing, shown in plot 602, or later (E to L), replication timing, shown in plot 604, occur in units of ~400-800 kb, smaller than static early or late domains and consistent with developmentally regulated changes in timing. FIG. 7 shows the percentage of the genome with significant timing changes toward earlier (L to E) or later (E to L) replication from the normal B-cell profiles in indicated cell types.

Replication Profiles Detect Karyotypic Abnormalities and Copy-Number Variation

Figure 8:
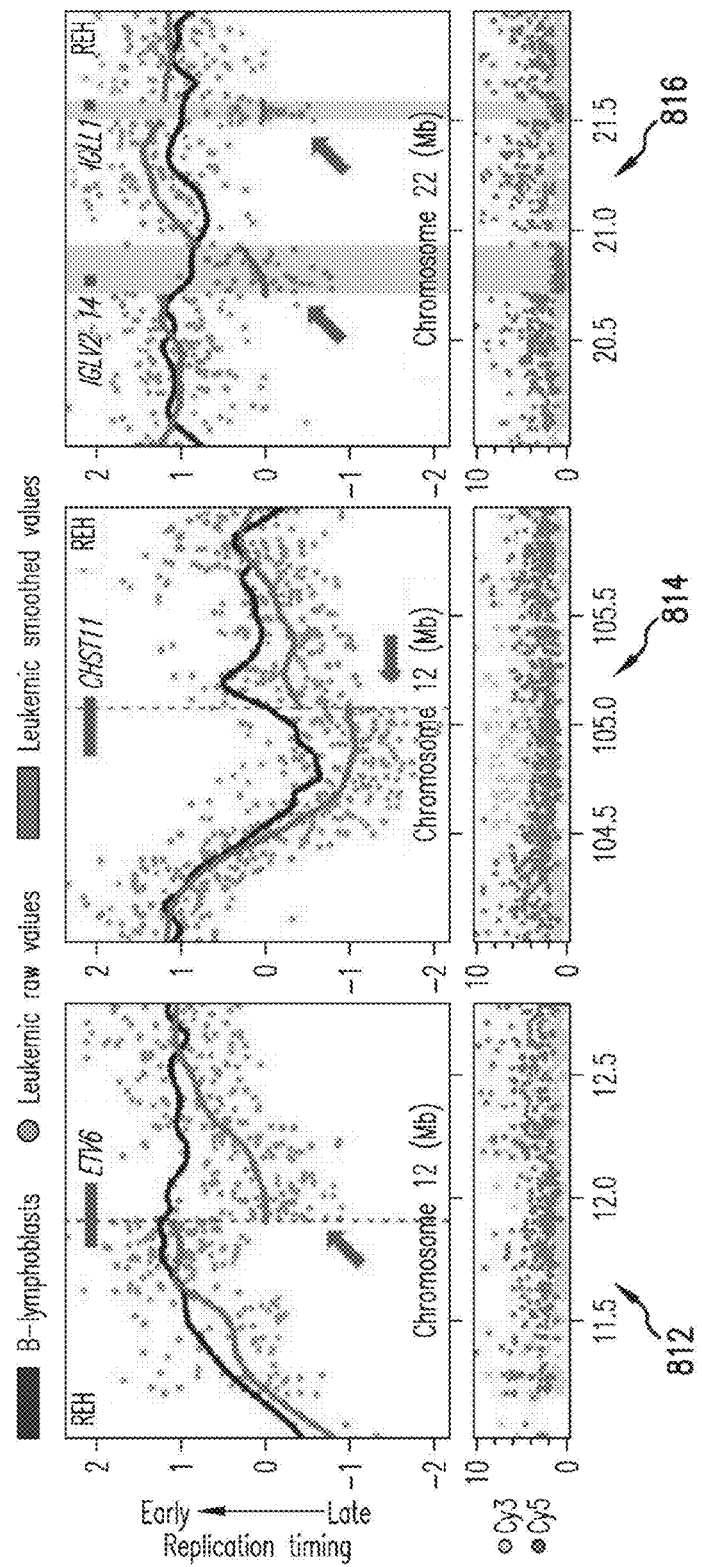
FIG. 8 shows plots of abrupt timing changes in replication timing in various regions of a chromosome.
Figures 9, 10:
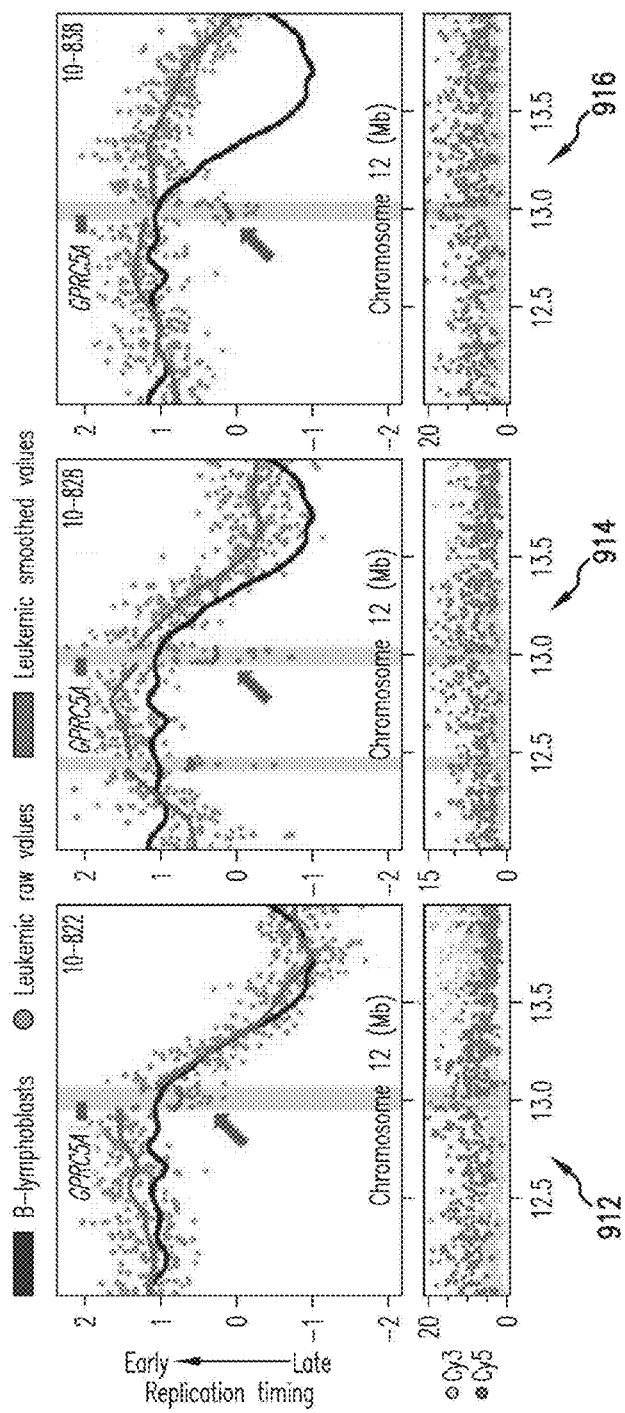
FIG. 9 shows plots of abrupt timing changes in replication timing in various regions of a chromosome.
FIG. 10 shows a summary of rearrangements detected in a cell line.

FIGS. 8, 9 and 10 illustrate abrupt shifts in replication timing localize a subset of rearrangements. Left plot 802 of FIG. 8 shows abrupt timing changes in REH at 12p13 map within ETV6 (TEL1) at 11.95 Mb, consistent with the molecularly mapped translocation site. Middle plot 804 of FIG. 8 shows a breakpoint at 12q23 (94.8-107.5 Mb) can be mapped more precisely within CHST11 by an abrupt shift in timing values at 105.08 Mb. Right plot 806 of FIG. 8 shows an abrupt timing changes in regions not included in published karyotypes of REH represent deletions of IGL loci involved in B-cell maturation, evidenced by a sharp drop in overall Cy5 and Cy3 signal intensity. FIG. 9 shows examples of abrupt timing changes in patients 10-822 (left plot 912), 10-828 (middle plot 914), and 10-838 (right plot 916) undetected by karyotype analysis, but suggesting a shared amplification of ~12.95-13.05 Mb in these three patients, which overlaps suspected tumor suppressor GPRC5A. FIG. 10 shows a summary of rearrangements detected in REH (left table 1012) and patient samples (right table 1014) by either CNV in raw replication-timing data or abrupt timing shifts lacking CNV (translocations). FIG. 10 shows a summary of the rearrangements illustrated in FIGS. S4, S5, S6, S7 and S8 of Reference 60).

Although >90% of mononucleate cells from bone-marrow aspirates are leukemic, only 5%-10% of cells were in S phase (Supplemental FIG. 2 of Reference 60. Hence, it was important to validate that these replication profiles were indeed derived from leukemic cells rather than proliferating contaminants. Most leukemias contain karyotypic abnormalities that distinguish them from contaminating cells (Supplemental FIG. 1 of Reference 60). Many of these lesions should be detectable in replication-timing data, serving as internal validation for the leukemic source of the replication-timing profiles. For example, aneuploidies were readily detectable as copy-number variation (CNV) derived from the sum of raw signal values (Cy3+Cy5) for probes encompassing those chromosomes (Supplemental FIG. 4 of Reference 60), providing validation for many samples.

The translocation breakpoints that juxtapose early and late-replication domains should be detectable as unnaturally sharp transitions in replication timing at the breakpoint where sequences are no longer in their original genomic position. As proof of principle a translocation in cell line REH for which the breakpoint junctions of both translocation partners have been precisely mapped was examined (Wiemels et al. 2000 (Reference 57)), a translocation that fuses the ETV6 (formerly TEL1) gene at 12p13 with RUNX1 (formerly AML1)

at 21q22. As shown in FIG. 8 this breakpoint was readily detected within ETV6 as an abrupt shift toward later replication timing that coincides with the molecularly mapped position of the breakpoint in REH. Downstream from the normally late-replicating RUNX1 partner, a shift to earlier replication also localized to the molecularly mapped breakpoint position (data not shown). Using this principle, it was possible to more precisely map an additional REH translocation that mapped cytogenetically between 94.8 and 107.5 Mb (Horsley et al. 2006 (Reference 24)) of 12q23 and by replication timing to 105.08 Mb (FIG. 8, middle plot 804). This locus is within the CHST11 gene that was found to be aberrant in other subtypes of leukemia (e.g., CLL) (Hiraoka et al. 2000 (Reference 20); Okuda et al. 2000 (Reference 39); Schmidt et al. 2004 (Reference 48)). Hence, this method was able to provide further validation of sample source (FIG. 10) and demonstrates that replication-timing data can facilitate the localization of translocation breakpoints. It should be noted that translocations that fuse loci with similar replication timing are not expected to produce abrupt shifts. This is consistent with results in patient 10-668, in which a Philadelphia chromosome translocation t(9;22)(q34;q11) fuses two regions that are normally late replicating, and remain late after translocation (data not shown).

Also found were abrupt timing shifts not represented by translocations in published karyotypes of REH (FIG. 8, right plot 806). Abrupt shifts in replication timing could also result from localized CNV. Amplifications could delay the time for replication forks to arrive to normally adjacent sequences and would appear as shifts toward later replication, while homozygous deletions would result in background levels of hybridization that would average to a log ratio of zero. Hence, abrupt shifts in replication-timing ratio data were computationally identified and determined whether each corresponded to significant CNV determined from raw array values (FIG. 8; Supplemental FIGS. 5, 6, 7 and 8 of Reference 60). A CNV was considered significant if it encompassed ≥2 probes within 10 kb with overall intensity outside of the 99.9th/0.1st percentiles. This analysis revealed that abrupt shifts in replication timing coinciding with sites of karyotypically defined translocations did not accompany significant CNV (FIG. 8, left plot 802, middle plot 804), whereas abrupt shifts that were not at known translocation sites represented either deletions or amplifications (FIG. 8, right plot 806; FIG. 9). For example, abrupt replication timing changes at 20.70-20.92 Mb and 21.49-21.59 Mb of Chr. 22 (FIG. 8, right plot 802), which include the IGLV2-14 and IGLL1 loci involved in B-cell maturation and often rearranged in leukemia (Tang et al. 1991 (Reference 53); Brauninger et al. 2001 (Reference 7)), are clearly due to large deletions encompassing those sequences that suddenly bring the replication-timing ratio to zero. Importantly, using algorithms and comparing the data to known CGH data for REH, it was possible to identify 79% of known gains (6/8), losses (30/37), and translocations (2/3) (FIG. 10, left table 1004). This appears to be an underestimate; since REH is an established cell line, it is possible that additional genetic changes exist between these cells and those that were analyzed for CGH.

Using these methods, it was possible to identify 87% of known karyotypic and genetic abnormalities from patient samples, providing important validation for the ability of replication timing to query proliferating leukemic cells directly from bone-marrow samples (FIG. 10, right table 1004; Supplemental FIGS. 4, 5, 6, 7 and 8 of Reference 60). However, as with REH, several examples of abrupt timing changes in patient samples at sites not detected as lesions in karyotypic data have been found, some of which were conserved among multiple samples of different ALL subtypes. For instance, samples 10-822, 10-828, and 10-838 all displayed a sharp shift to later replication at the same location near 12.95 Mb on chromosome 12, but did not show karyotypic abnormalities at this site (in fact, 10-838 showed a normal karyotype). In all three cases, this replication-timing change was associated with a gain in copy number (FIG. 9). Intriguingly, this locus is within suspected tumor-suppressor gene GPRCSA (Tao et al. 2007 (Reference 54); Acquafreda et al. 2009 (Reference 1)), suggesting the possibility that persistent STAT3 activation due to mutation of GPRCSA (Chen et al. 2010 (Reference 10)) may be a contributing factor in these patients. Interestingly, both samples 10-822 [carrying the t(17;19)] and 10-838 were from relapsed patients who eventually died of their disease, suggesting that GPRCSA disruption should be investigated for potential prognostic significance. The break region also contains a binding site for the B-cell CLL/lymphoma 11A (BCL11A) protein, which mediates gamma-globin expression and blood-cell maturation through long-range chromatin interactions (Xu et al. 2010 (Reference 58)).

Taken together, it may be concluded that genome-wide replication timing profiles generated from bone-marrow samples of leukemia patients accurately reflect the replication program of their leukemic cells. Moreover, they simultaneously report on both replication-timing abnormalities and CNV. It can be estimated that, depending on the timing difference between the regions and the proportion of cells with the translocation, at least 30%-50% of translocations and 75% of CNVs will be detectable from replication-timing profiles (FIG. 10; Supplemental FIGS. 4, 5, 6, 7 and 8 of Reference 60). Moreover, replication timing analyses reveal long-range influences of a breakpoint on replication timing, which may propagate hundreds of kilobases from the break site, and such changes would not be detected by conventional CGH or genome sequencing. Such distal changes could be very important. For example, deregulation of genes hundreds of kilobases from a common breakpoint in an a plastic large cell lymphoma (ALCL) has been shown to play a causal role in ALCL (Mathas et al. 2009 (Reference 34)).

Patient-Specific Epigenetic Replication-Timing Fingerprints

Figure 11:
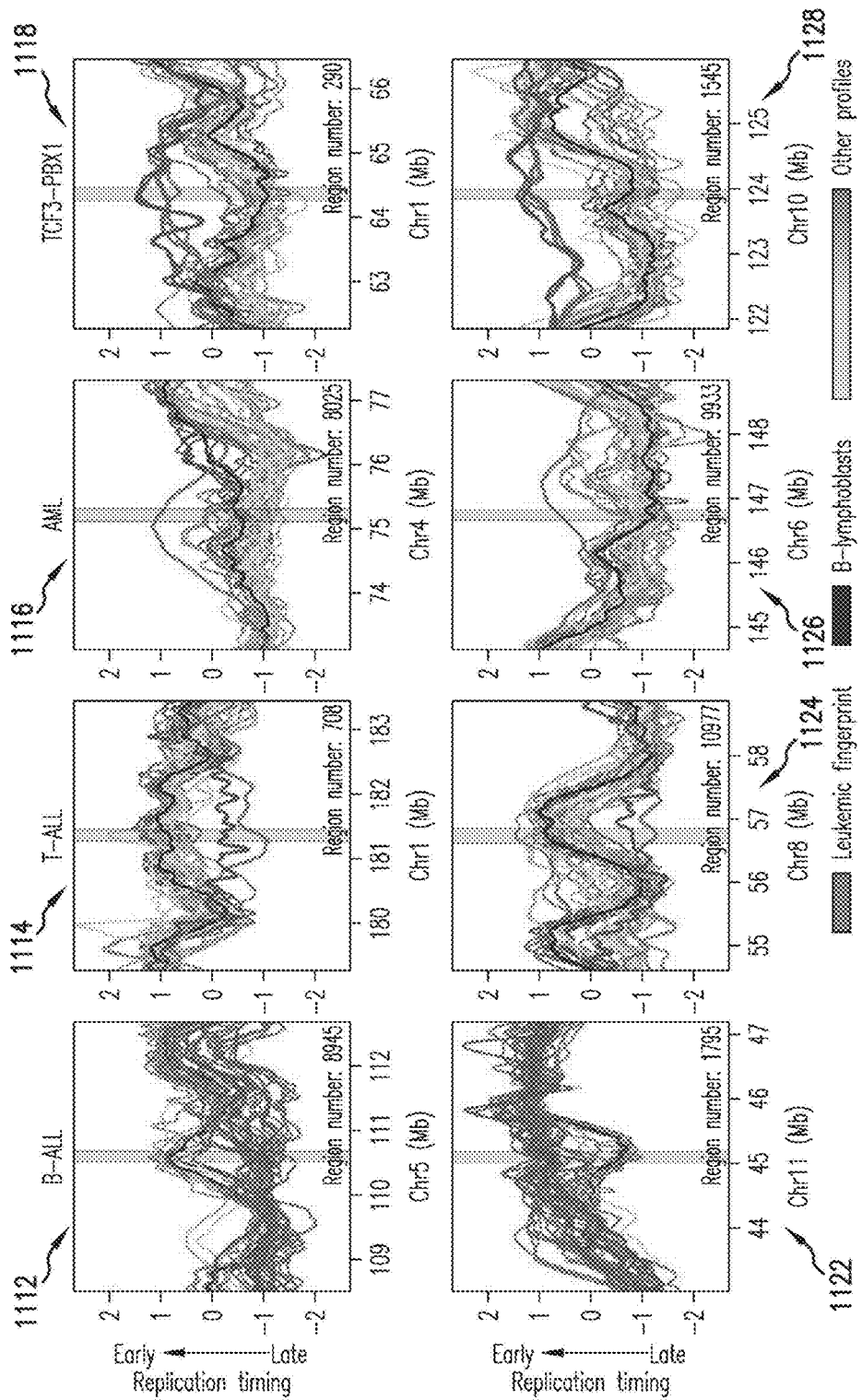
FIG. 11 illustrates leukemia type-specific replication-timing differences.

FIG. 11 illustrates leukemia type-specific replication-timing differences. Example fingerprint regions 1112, 1114, 1116, 1118, 1122, 1124, 1126 and 1128 depict leukemia type-specific timing differences in B-cell ALL (fingerprint regions 1112 and 1122), T-cell ALL (fingerprint regions 1114 and 1124), AML (fingerprint regions 1116 and 1126), and TCF3/PBX1 (fingerprint regions 1118 and 1128) translocation-positive cell lines and patient samples. Colors correspond to the color key at right, with colors of fingerprint profiles highlighted in red, indicated by arrow 1132, other profiles in gray, indicated by arrow 1134 and an average of karyotypically normal B-cell controls in black, indicated by arrow 1136. Tables of fingerprint regions and genes are given in Supplemental Table 2 of Reference 60.

The premise for this study was to test the hypothesis that, just as specific cell types display unique epigenetically regulated replication-timing fingerprints, cancers might display their own class of epigenetic replication-timing differences. These replication-timing "fingerprints" can be identified using a previously described replication-fingerprinting algorithm (Ryba et al. 2011b (Reference 46)), which isolates regions of unique replication timing between any predesignated sets of samples. As shown in FIG. 11, different classes of leukemia can be distinguished by their common differences in replication timing from all other samples. Replication fingerprints found only in B-ALL (n=16), T-ALL (n=2), AML (n=1), or patients and cell lines with TCF3/PBX1 translocations (n=2) were identified. A complete list of these fingerprints can be found in Supplemental Table 2 of Reference 60. As expected from FIGS. 1, 2, 3 and 4, comparison to normal mature human CD4+ T cells verified that some T-ALL-specific fingerprints were likely due to normal developmental differences. Without access to normal human proliferating immature lymphoblasts, it is difficult to rule out the possibility that any individual feature of the fingerprint may reflect arrest at a particular stage of immature B-cell development. However, a much higher proportion of differences from B-cell controls were shared between B-ALL and T-ALL than were exclusive to either one, suggesting that many differences from controls were not due to the developmental stage of the leukemias, and at least some were common to all leukemias (discussed below).

Figure 12:
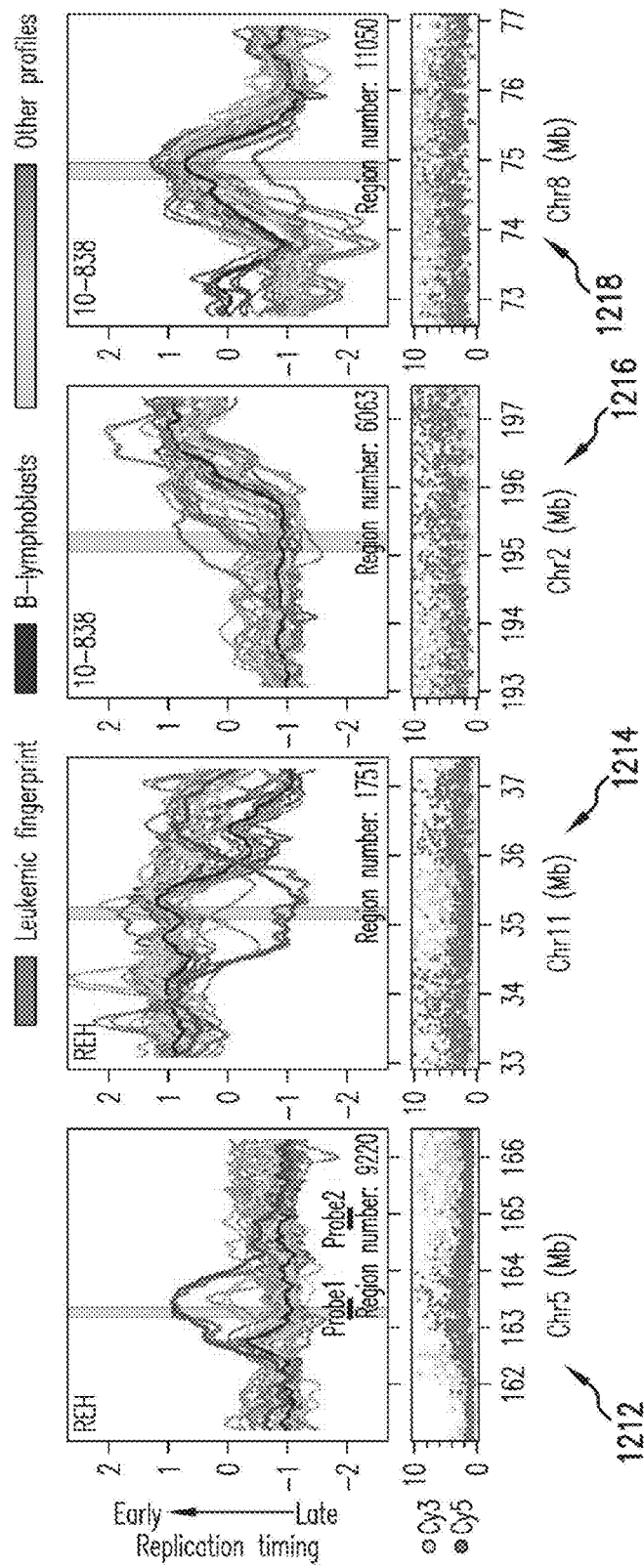
FIG. 12 shows sample-specific fingerprint regions in a cell line and a patient.

Fingerprinting identifies a small number (~20) of the largest replication-timing differences. This contrasts with hierarchical clustering, which highlights widespread but small differences in replication timing across the genome. For example, in FIGS. 5, 6 and 7, patients 10-838, 11-118, 11-220, 11-132, 10-820, 11-015, 11-253, and 10-668 clustered together, but it was not possible to find a well-defined fingerprint able to distinguish this group of patients from all others. Importantly, the criteria for fingerprinting largely excluded changes associated with genetic lesions. In fact, using the criteria provided in the descriptions of FIGS. 8, 9 and 10, >74% of fingerprint regions did not exhibit CNV or abrupt changes in Cy3/Cy5 ratios 61 Mb from the fingerprint region (e.g., FIG. 16). Due to their lack of association with genetic changes detectable by karyotype or CNV analysis, these replication timing fingerprints may be referred to as "epigenetic replication timing fingerprints" (albeit, genetic changes that do not affect CNV or replication time such as inversions within regions of constant replication timing would not be detected). Some epigenetic fingerprints were specific to a single cell line or patient sample (FIG. 12). These changes may serve as unique identifiers of the different patient leukemias regardless of whether they represent arrested development or are causally linked, and should be pursued for their potential as biomarkers for risk stratification.

Figure 13:
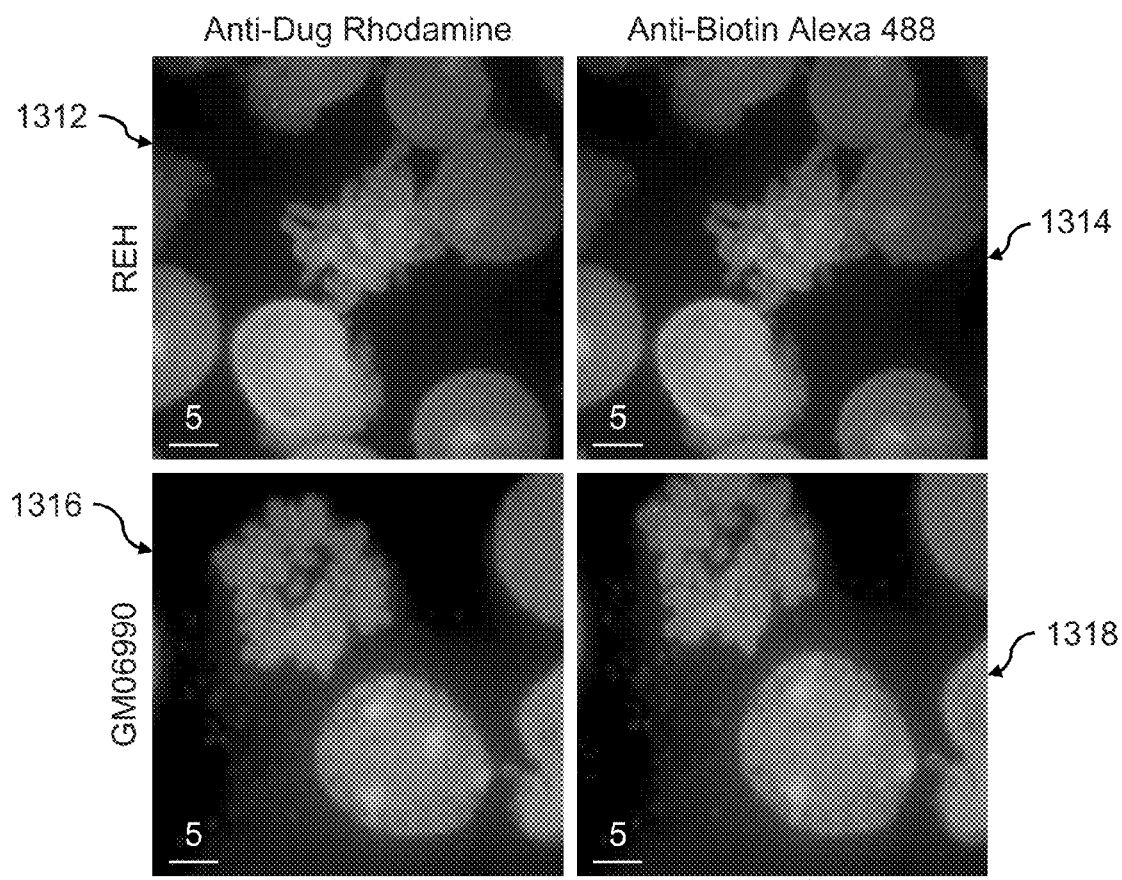
FIG. 13 shows fluorescent in situ hybridization images of two cell lines showing region-specific binding in metaphase nuclei and doublet/singlet hybridization patterns in interphase nuclei.
Figures 14, 15:
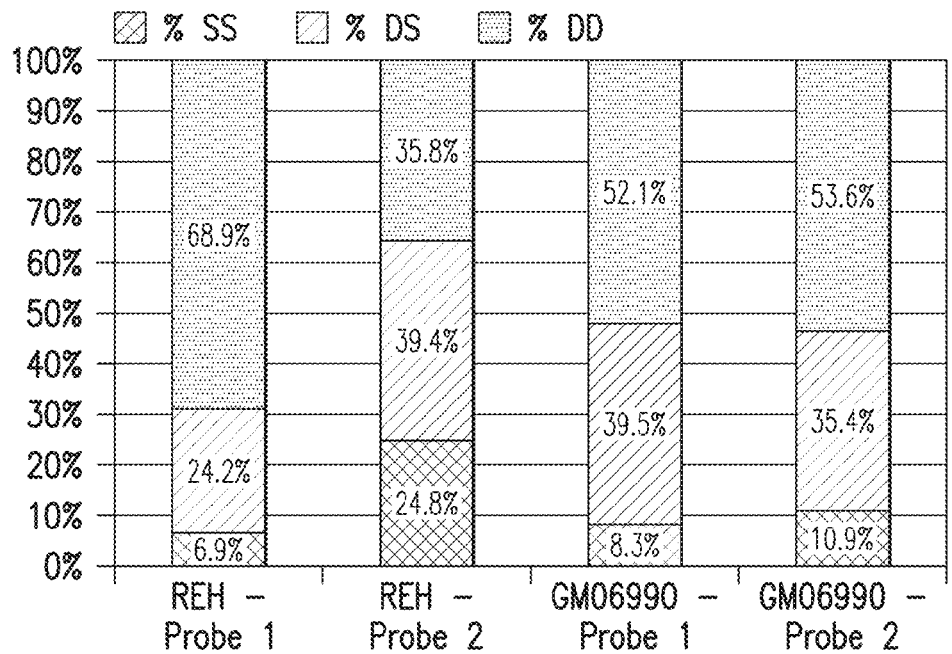
FIG. 14 illustrates quantification of observed singlet/singlet (SS), doublet/singlet (DS), and doublet/doublet (DD) configuration of allelic homologs for each probe shown in FIG. 12.
FIG. 15 illustrates the quantification of the frequency with which one probe appeared to replicate prior to the other as a percentage of total chromosomes scored.

To verify these findings by an independent method, one of the replication-timing changes specific to the cell line REH was analyzed by the singlet-doublet DNA replication assay (FIGS. 13, 14 and 15).

FIGS. 12, 13, 14 and 15 illustrate replication-timing differences in karyotypically normal regions. FIG. 12 shows sample-specific fingerprint regions in cell line REH (fingerprint regions 1212 and 1214) and patient 10-838 (fingerprint regions 1216 and 1218) that lack genetic lesions under karyotypic analysis (both samples, with 10-838 being karyotypically normal), total Cy3+Cy5 intensity (both samples) or Sanger CGH (REH), and therefore represent apparently epigenetic timing changes. Such regions may be explained by changes in long range interactions or by subkaryotypic or CGH-resolution rearrangements. As in FIG. 11, fingerprint profiles (REH or 10-838) are highlighted (red, indicated by arrow 1132) against a background of other leukemic samples (gray, indicated by arrow 1134) and B-lymphoblastoid cells (black, indicated by arrow 1134). FIG. 13 shows fluorescent in situ hybridization images of cell lines REH (images 1312 and 1314) and GM06990 (images 1316 and 1318) showing region-specific binding in metaphase nuclei and doublet/singlet hybridization patterns in interphase nuclei. FIG. 14 illustrates quantification of observed singlet/singlet (SS), doublet/singlet (DS), and doublet/doublet (DD) configuration of allelic homologs for each probe shown in FIG. 12. Only nuclei displaying at least one doublet allele (189 GM06990 and 296 REH) in either probe were scored, which may exaggerate the percentage of nuclei that appear to have replicated the regions asynchronously (single-doublets). FIG. 15 illustrates the quantification of the frequency with which one probe appeared to replicate prior to the other as a percentage of total chromosomes scored for which cis-linked probes 1 and 2 show a singlet-doublet configuration (378 GM06990 and 592 REH). In REH, probe 1 appears to replicate prior to probe 2 nearly 75% of the time, whereas in GM06990 either probe may replicate first.

After cellular fixation methods that separate sister chromatids, fluorescence in situ hybridization (FISH) reveals replicated homologs as doublet signals in the nucleus, while unreplicated homologs appear as singlets. These results confirmed that the REH-specific fingerprint region displayed a substantially higher frequency of doublets than the same region in nonleukemic GM06990 or than an adjacent region that replicates late in both normal and leukemic cells. This result was further con-firmed through replication timing in situ hybridization (ReTiSH) (Schlesinger et al. 2009 (Reference 47); Supplemental FIG. 9 of Reference 60)

A "Pan-Leukemia" Replication-Timing Fingerprint

Figure 16:
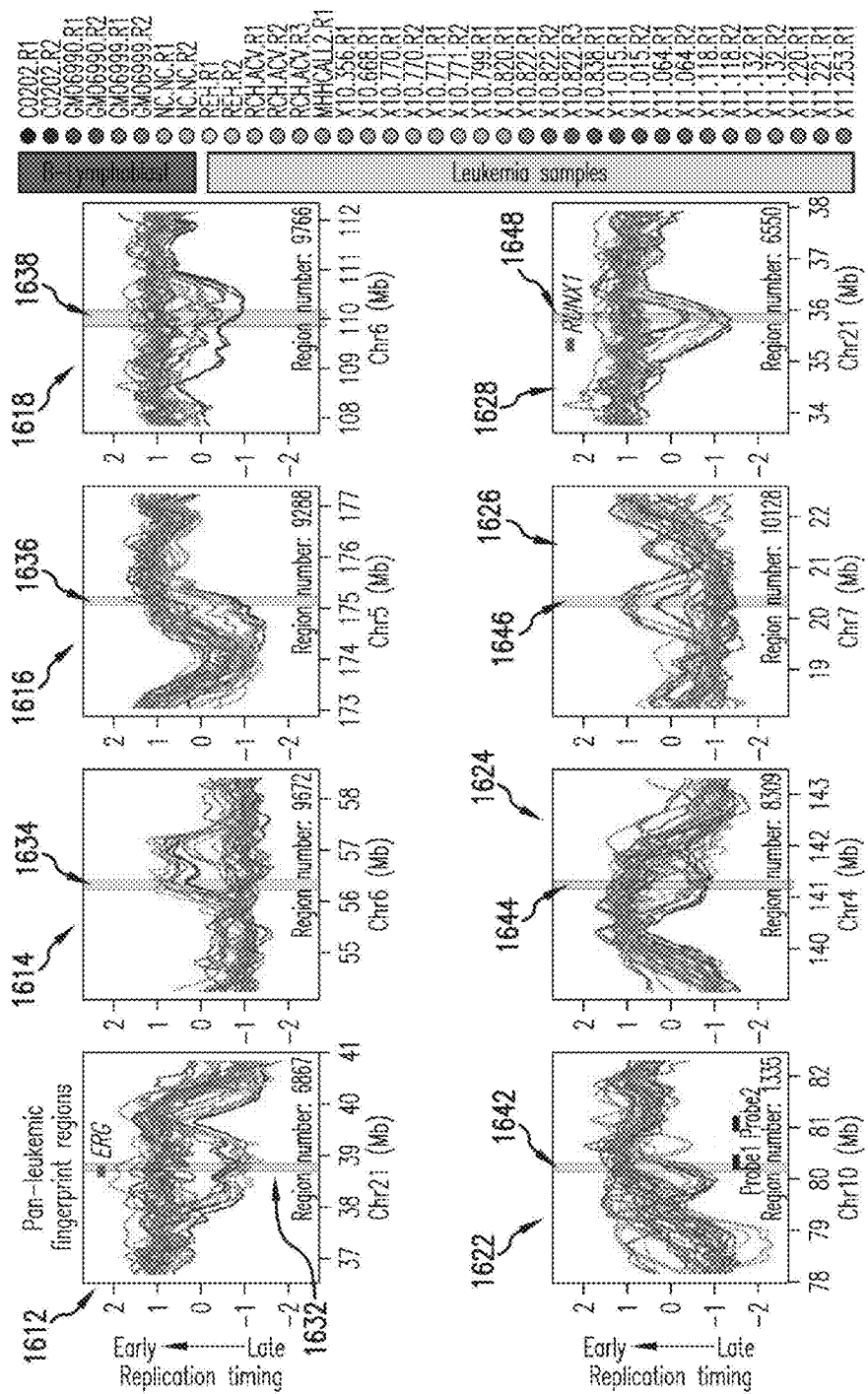
FIG. 16 shows example regions from a pan-leukemic fingerprint between all leukemic cells versus B-cell controls.
Figures 17, 18:
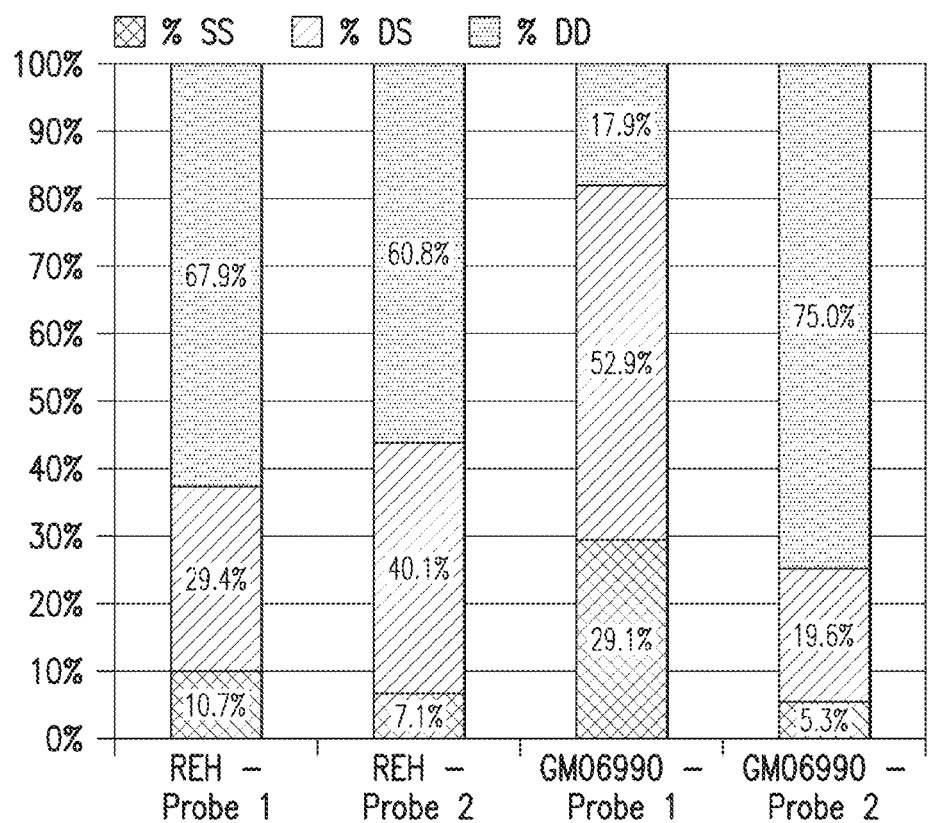
FIG. 17 shows the percentages of SS, DS, and DD configurations for each of the FISH probes indicated in FIG. 16.
FIG. 18 illustrates the quantification of the frequency with which one probe appears to replicate prior to the other as in FIG. 15.
Figure 19:
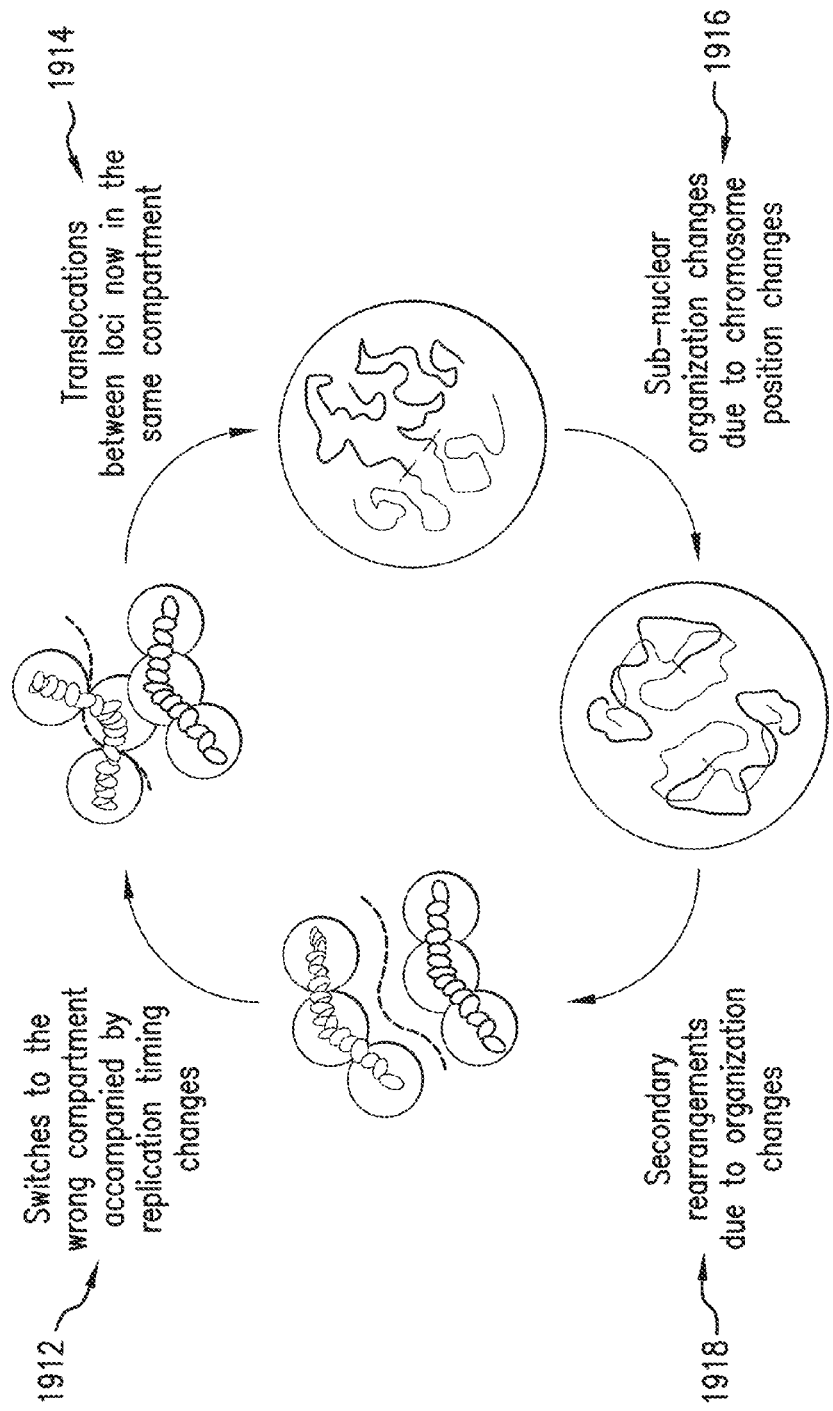
FIG. 19 illustrates a prospective model for common early events in leukemogenesis.

FIGS. 16, 17, 18 and 19 illustrate pan-leukemic replication-timing changes suggest common early events in leukemogenesis. FIG. 16 shows example regions 1612, 1614, 1616, 1618, 1622, 1624, 1626 and 1628 from a pan-leukemic fingerprint between all leukemic cells versus B-cell controls. Fingerprint regions are highlighted in respective gray overlays 1632, 1634, 1636, 1638, 1642, 1644, 1646 and 1648. FIG. 17 shows the percentages of SS, DS, and DD configurations for each of the FISH probes indicated in FIG. 16, as probes 1 and 2 were scored as in FIG. 14 (192 GM06990 and 516 REH nuclei scored). FIG. 18 illustrates the quantification of the frequency with which one probe appears to replicate prior to the other as in FIG. 15 (384 GM06990 and 1032 REH chromosomes scored). FIG. 19 illustrates a prospective model for common early events in leukemogenesis. In step 1912 loci in late-replicating compartments on the periphery undergo a switch to earlier replication together with a switch to the wrong nuclear compartment, which may be precipitated by loss of anchorage on the periphery or incorporation of accessibility-promoting chromatin factors in early-S phase. In step 1914 translocations occur between loci that now occupy the same compartment. In step 1916 Large rearrangements between chromosomes disrupt the normal distribution of chromatin in the nucleus, leading to further subnuclear organization changes. In step 1918 subnuclear organization changes bring together additional loci that would normally not be in contact or share the same compartment, leading to accumulation of additional secondary rearrangements and genome instability.

Many replication-timing changes were found to be in common between all leukemia cells, referred to as "pan-leukemic fingerprints" (FIGS. 16, 17 and 18). These changes are unlikely to be the result of differences in the developmental stage of the ALL samples vs. the B-cell baseline, as they were also found in the few T-ALL and AML samples that have been profiled, but may represent early events in leukemogenesis (FIG. 19). Since each type of leukemia has a different genetic constitution, panleukemic changes are likely to be epigenetic in origin in most leukemias. One such aberration is located at the RUNX1 locus (FIG. 16), at the site of the ETV6/RUNX1 translocation that in this study was found in the cell line REH and several patient samples, and which causes a large shift from late to early replication over several hundred kilobases.

Intriguingly, every leukemic cell type profiled had this same extensive replication-timing fingerprint, terminating at the same boundaries, independent of the breakpoint. This finding indicates that the replication-timing change reflects an epigenetic misregulation that precedes (possibly predisposes) breakage at this site and that the replication-timing domain boundaries—rather than the site of translocation—determine the range of influence (FIG. 19). The RUNX1 gene is thought to be involved in normal hematopoiesis and is one of the most frequently disrupted genes in leukemia (Niebuhr et al. 2008 (Reference 38)). These observations support the hypothesis that RUNX1 serves a gate keeping function for leukemia (Niebuhr et al. 2008 (Reference 38) and suggest that the pan-leukemic replication-timing finger print may be related to the disease state due to an epigenetic phenomenon rather than a mutation or translocation.

Other interesting examples in the pan-leukemic fingerprint include a region downstream from the RUNX1 gene at ~39 Mb on chromosome 21 in all leukemic cell types profiled (FIG. 16). Like the RUNX1 region, this region is much earlier replicating than control B cells in all leukemic cell types. Interestingly, this region contains the ERG gene, which is involved in hematopoietic regulation and chromosomal translocations in other types of cancer, including AML (Marcucci et al. 2005 (Reference 33). Another example is a region of the extended MHC (Major Histocompatibility Complex) that harbors two gene clusters: the BTN (butyrophilin) and the major histone gene cluster, HIST1. The BTN cluster contains a total of seven genes, including the BTN1A1 gene, and the two subfamilies BTN2 and BTN3, each of which contain three genes (Rhodes et al. 2001 (Reference 43)). The precise role of these genes in immune response is unknown, but BTN1A1 and the BTN2 genes have been implicated as negative regulators of T-cell activation (Smith et al. 2010 (Reference 50)). BTN3 mRNA is widely expressed in immune cells such as T cells, B cells, macrophages, dendritic cells, and monocytesm with most protein expression occurring at the cell surface (Rhodes et al. 2001 (Reference 43); Compte et al. 2004 (Reference 12); Smith et al. 2010 (Reference 50)). Additionally, most members of the BTN family contain a 30.2 protein domain, which is a 170-amino acid globular domain found at the C terminus of proteins for which there is evidence of involvement in inflammatory response (Compte et al. 2004 (Reference 12)). The histone gene cluster contains a total of six genes, HIST1H4H, HIST1H2BI, HIST1H3G, HIST1H2BH, HIST1H3F, and HIST1H4G. Interestingly, this gene cluster is also present in a group of replication-timing fingerprints specific to pluripotent cell types (Ryba et al. 2011b (Reference 46). Finally, to confirm predictive ability of the pan-leukemic fingerprint for new samples, a leave-one-out cross-validation (LOOCV) as described (Ryba et al. 2011b (Reference 46)) was applied to predict the identity of each sample using regions selected in the absence of that sample. In this test, leukemic/nonleukemic identity was accurately assessed in 40/40 test cases, and 87% of fingerprint regions were conserved throughout cross-validation. A complete list of the pan-leukemic fingerprint regions can be found in Supplemental Table 2 of Reference 60.

Figures 20, 22:
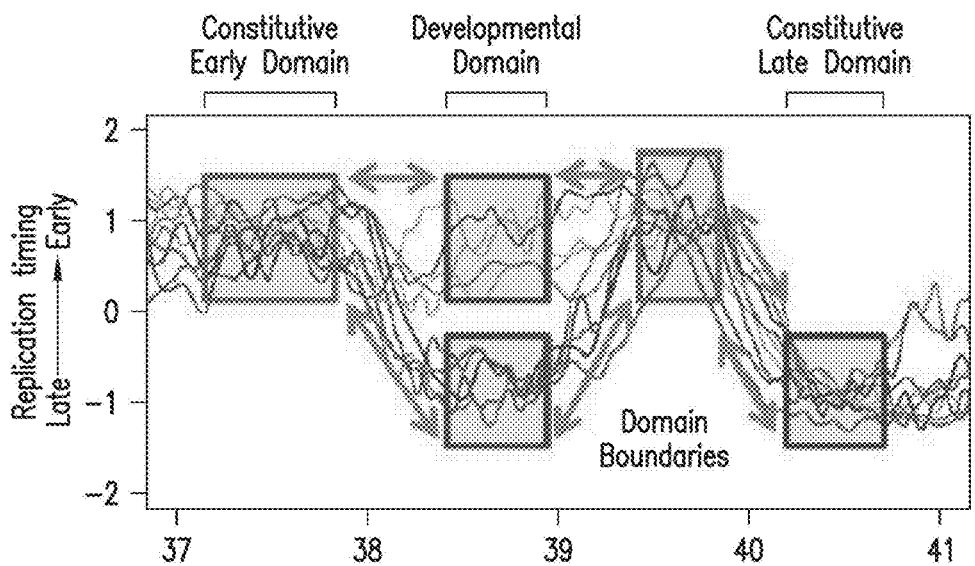
FIG. 20 is a diagram of normal boundaries of replication in development.
FIG. 22 shows a summary of the number of domains in leukemic fingerprints that align to developmental boundaries.
Figure 21:
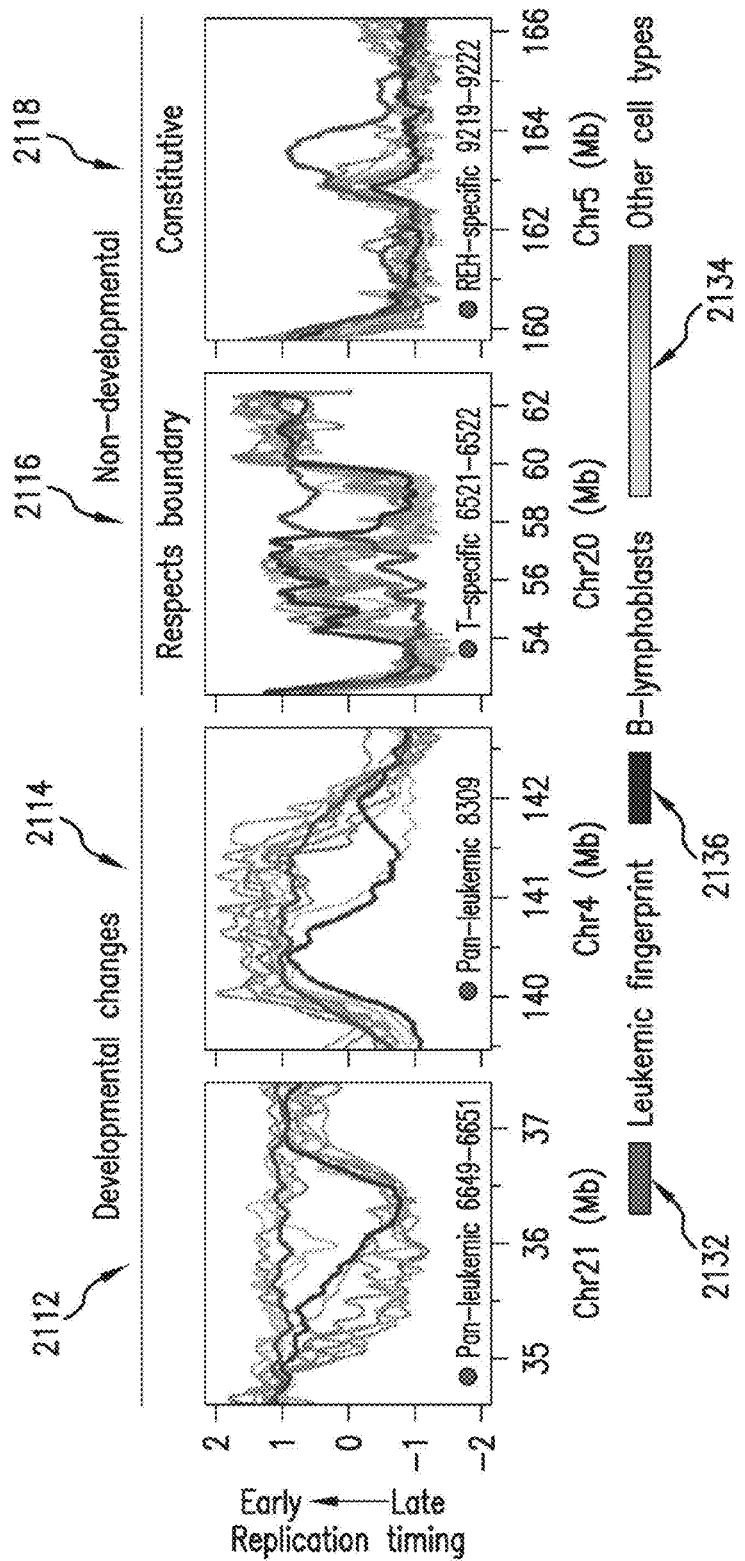
FIG. 21 shows examples of each class of domains in leukemic fingerprints that switch replication timing against a background of other human cell types and normal B-cell controls.

Replication-Timing Fingerprints Align with Developmentally Regulated Replication Domains FIGS. 20, 21 and 22 illustrate replication changes in leukemia respect normal developmental boundaries. FIG. 20 is a diagram of normal boundaries of replication in development, defining regions of constitutively early or late replication timing, conserved boundaries between these regions, and developmentally regulated domains. FIG. 21 shows examples, i.e., exmaples 2112, 2114, 2116 and 2118, of each class of domains in leukemic fingerprints that switch replication timing (red, indicated by arrow 2132) against a background of other human cell types (gray, indicated by arrow 2134) and normal B-cell controls (black, indicated by arrow 2136). Here, two pan-leukemic fingerprint regions align to both developmental boundaries and timing values. T-cell profiles switch timing in opposite directions from others, but at the same transition region as is used in B cells and other cell types, while an REH-specific fingerprint region aligns to one boundary but switches earlier than other cell types profiled. Additional examples of domain boundary alignment are shown in Supplemental FIG. S10 of Reference 60. FIG. 22 shows a summary of the number of domains in leukemic fingerprints that align to developmental boundaries, either with or without acquiring the timing of other cell types.

Replication-timing fingerprints are of the same size range as normal developmentally regulated replication domains (FIG. 6). This raised the possibility that they represent misregulation of developmental control over replication timing, as has been described for DNA methylation changes in cancers (Hansen et al. 2011 (Reference 19); Pujadas and Feinberg 2012). To test this hypothesis, the collection of leukemia fingerprints were compared with profiles of the same genomic regions from nine cell types that have been profiled in the past (Weddington et al. 2008 (Reference 56); Pope et al. 2011 (Reference 40); Ryba et al. 2011b (Reference 46). More than half of these aligned in register to a developmentally regulated replication domain boundary (FIGS. 20, 21 and 22; Supplemental FIG. 10 of Reference 60). The remaining half of the fingerprints shared boundaries present in all queried cell types, or in rare cases appeared to create a new boundary within a large early- or late-replicating region. These latter cases could be developmental replication-timing boundaries in cell types that have not been queried. Importantly, in no case did a leukemia fingerprint boundary pass over a developmental boundary or appear in a novel position out of register with a known boundary. These results indicate that the replication-timing differences that distinguish leukemias from each other and from normal cell types are the same units of chromosomes that distinguish cell types from each other. Interestingly, however, the cohort of fingerprints for any particular leukemia correlated poorly (R=0.43–0.61) with that of any profiled human cell type (Ryba et al. 2011b (Reference 46), indicating that leukemias do not take on the identity of any particular cell type, but acquire misregulated features of many different cell types.

Discussion

Here it is shown that genome-wide replication-timing analyses detect widespread deregulation of replication timing in leukemias. While control cell lines show remarkably stable and cell-type specific replication profiles, leukemic samples deviate substantially from controls and from each other, demonstrating a high degree of instability in the replication program. These differences occurred largely in units of 400-800 kb and align with developmentally programmed changes in replication timing, supporting the concept of the replication domain as a unit of chromosome structure and function and suggest that mechanisms acting at the level of these units are misregulated in cancer. Despite their heterogeneity, leukemic cells all share certain replication-timing aberrations, indicating common early events in leukemogenesis that appear to be conserved. Some of these commonalities occur at sites of translocations but are remarkably identical independent of the translocation, suggesting that the changes precede the translocation and that the distance over which replication timing is influenced is determined by misregulation of replication-timing domains rather than by the site of translocation.

These results provide the first comprehensive assessment of replication misregulation in cancer, identify novel epigenetic events occurring early in leukemogenesis, and suggest the possibility that specific subtypes of leukemia may be linked to specific replication-timing fingerprints that should be pursued for their potential as a novel genre of cancer biomarkers.

Genome-wide assessments of transcription, sites of DNA methylation, and the distribution of chromatin proteins and their modifications have received a lot of recent attention and offer great promise (Bibikova et al. 2006 (Reference 5)). However, each is informative for only the fraction of the genome affected by each property and some of these methods are expensive and laborious. Replication profiles comprehensively and reliably assess epigenetic state genome wide, and are considerably less expensive to generate and easier to interpret than these other markers. Full genome-scale profiling can be performed with less than a million cells (Gilbert 2010 (Reference 18); Hiratani et al. 2010 (Reference 23)). Analysis of replication timing is fundamentally different from other common genome wide methodologies in that it queries large-scale organization of the genome, which has otherwise been assessed only through challenging chromatin-conformation capture methods (Lieberman-Aiden et al. 2009 (Reference 30)). In fact, the uncanny alignment of replication timing to existing chromatin interaction maps (Ryba et al. 2010 (Reference 44)) implies that replication-timing profiles predict megabase-level spatial organization of chromosomes. Hence, replication-timing changes likely reflect novel spatial relationships (e.g., unusual juxtapositions of chromosome segments) that may predispose cells to particular translocation events. Consistently, a recent analysis found significant linkages between cancer rearrangements and replication timing (De and Michor 2011 (Reference 15)). Hence, replication-timing abnormalities have the potential to inform early cancer diagnosis.

In translocations between temporally distinct replication domains, replication timing will necessarily change across hundreds of kilobases. Since different types of chromatin are assembled at different times, this may transmit chromatin changes long distances from the break site. In fact, attempts to implicate the gene loci near translocation breakpoints in the etiology of the associated cancer have met with limited success (Hunger et al. 1998 (Reference 26); Strefford et al. 2009 (Reference 51) Hence, replication profiling has the potential to detect long-range effects of a chromosome break. In addition, complex genome rearrangements smaller than ~1 Mb that do not alter copy number, such as inversions, will escape detection by both spectral karyotyping and comparative genomic hybridization (CGH) methods, but may replicate at a distinctly different time from their native location. Finally, most of the replication-timing differences that have now been identified between leukemias are unlikely to be associated with any genetic lesion and would not be detected by any other current method. At present, the significance of replication-timing changes to the cancer phenotype is unknown. There is a general correlation between replication timing and gene expression, but it is promoter specific and appears to reflect transcriptional competence rather than transcription per se (Hiratani et al. 2009 (Reference 22)). The similarity in sizes of replication domains and regions of long-range epigenetic silencing (LRES) that has been observed in many cancers (Coolen et al. 2010 (Reference 13); Hsu et al. 2010 (Reference 25); Dallosso et al. 2012 (Reference 14)) and the observation that LRES consolidates the cancer genome to reduce transcriptional plasticity while replication timing consolidates during differentiation (Hiratani et al. 2008 (Reference 21)), suggest a potential relationship between these mechanisms. Taken together, replication profiling can identify novel genetic lesions and their associated long-range effects, as well as epigenetic changes that escape detection by other diagnostic methods.

Methods

Cell Lines and Culture

Sources of control cells lines CO202, GM06990, GM06999, and NC-NC are provided in Supplemental FIG. 1 of Reference 60. Cell lines REH, RCH-ACV, and CALL-2 were purchased from ATCC. Cells were cultured in standard media of RPMI with 10% fetal bovine serum, 4 mM glutamine, 1% penicillin, and streptomycin.

Sample Collection

Patient bone-marrow samples were collected as part of ongoing clinical trials at OHSU from patients who consented for enrollment in biologic studies. Currently, patients <21 yr of age with suspected leukemia are eligible for enrollment for biologic studies at the Oregon Health & Science University (OHSU) with Institutional Review Board Approval. In most cases of newly diagnosed pediatric ALL, a bone-marrow aspiration is performed to confirm the diagnosis. Samples from subjects on the biologic study were assigned a unique identifier for health information protection. Subjects include all genders, minorities, and children eligible for the study. Bone-marrow aspirate generally contains close to 1 3 106 cells/mL and is usually >80% lymphoblasts. Other fresh bone-marrow samples were obtained from the Children's Oncology Group (COG) ALL Cell Bank for a pilot study. These fresh samples were processed to purify mononuclear cells by centrifugation through Ficoll. The mononuclear cell ring was then isolated and counted. Then, 0.5-1 3 107 cells were labeled with 10 mg/mL BrdU for 2 h in RPMI, 10% FBS media, fixed in 70% ethanol, and shipped to FSU.

Genome-Wide Replication-Timing Analysis

Genome-wide replication timing was analyzed as described in detail (Ryba et al. 2011a (Reference 45)) using NimbleGen HD2 arrays (3 3 720 K format) with average interprobe spacing of 2509 bp. Probes were designed against build Hg18 (NCBI 36) of the human genome.

Computational Methods

Replication-timing data were normalized within and between arrays using the limma package in R, and smoothed using loess with a span of 300 kb, as described (Ryba et al. 2011a (Reference 45)). To quantify the relative percentage of the genome with significant changes in timing, the fraction of loess-smoothed points with RT value differences of 1 or greater were calculated. For clustering and fingerprint analysis, data were averaged into nonoverlapping 200-kb windows, and replication fingerprints were created as described (Ryba et al. 2011b (Reference 46)) to identify regions of shared replication-timing changes in defined groups of samples. Hierarchical clustering was performed using the pvClust package in R with absolute correlation as a distance metric. Methods for CNV detection were applied using the CGHweb R package and R/Bioconductor scripts to identify regions encompassing $2 probes within 10 kb, with overall intensity outside of the 99.9 th/0.1st percentiles.

Methods and techniques, including techniques and methods conducted manually ad/or by a computer, that may be employed in various embodiments of the present invention to determine that a population of cells are a specific type of leukemic cells based on a replication timing fingerprint are described in U.S. patent application Ser. No. 13/479,686 to Gilbert et al., entitled "GENOME-SCALE ANALYSIS OF REPLICATION TIMING," filed May 24, 2012 and the entire contents and disclosure of this patent application are incorporated herein by reference. The methods and techniques described in Gilbert et al. that may be employed in various embodiments of the present invention include but are not limited to obtaining replication timing profiles using a high resolution genomic array, determining one or more replication timing fingerprints of a cell by comparing replication domain timing profiles, the computer-assisted identification and characterization of replication domains and their properties (e.g., chromosomal position, length, boundaries, etc.) for a population of cells based on the replication timing profile for the population of cells, etc.

Techniques and materials that may be used in various embodiments of the present invention are described in Ryba, T., Battaglia, D., Chang, B. H., Shirley, J. W., Buckley, Q., Pope, B. D., Devidas, M., Druker, B. J., and Gilbert D. M. "Abnormal developmental control of replication-timing domains in pediatric acute lymphoblastic leukemia," *Genome Res.* 22(10):1833-44 (2012), the entire contents and disclosure of which are incorporated herein by reference.

All documents, patents, journal articles and other materials cited in the present application are incorporated herein by reference.

Having described a particular embodiment of the present invention, it will be apparent that modifications and variations are possible without departing from the scope of the invention defined in the appended claims. Furthermore, it should be appreciated that the example provided in the present disclosure, while illustrating a particular embodiment of the invention, is provided as a non-limiting example and is, therefore, not to be taken as limiting the various aspects so illustrated.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

REFERENCES

The following references are referred to above and are incorporated herein by reference:

1. Acquafreda, T., Soprano, K. J., Soprano D. R. "GPRC5A: A potential tumor suppressor and oncogene" *Cancer. Biol. Ther.* 8: 963-65 (2009).
2. Adolph, S., Hameister, H., Schildkraut, C. L. "Molecular analysis of the aberrant banding pattern on chromosome 15 in murine T-cell lymphomas." *Chromosoma* 101: 388-98 (1992).
3. Amiel, A., Elis, A., Sherker, S., Gaber, E., Manor, Y., Fejgin, M. D. "The influence of cytogenetic aberrations on gene replication in chronic lymphocytic leukemia patients." *Cancer Genet. Cytogenet.* 125: 81-86 (2001).
4. Amiel, A., Elis, A., Maimon, O., Ellis, M., Herishano, Y., Gaber, E., Fejgin, M. D., Lishner, M. "Replication status in leukocytes of treated and untreated patients with polycythemia vera and essential thrombocytosis." *Cancer Genet. Cytogenet.* 133: 34-38 (2002).
5. Bibikova, M., Chudin, E., Wu, B., Zhou, L., Garcia E. W., Liu, Y., Shin, S., Plaia, T. W., Auerbach, J. M., Arking, D. E., et al. "Human embryonic stem cells have a unique epigenetic signature." *Genome Res* 16: 1075-83 (2006).
6. Bienz, M., Ludwig, M., Leibundgut, E. O., Mueller, B. U., Ratschiller, D., Solenthaler, M., Fey, M. F., Pabst, T. "Risk assessment in patients with acutemyeloid leukemia and a normal karyotype." *Clin. Cancer Res.* 11: 1416-24 (2005).
7. Brauninger, A., Goossens, T., Rajewsky, K, Kuppers, R. "Regulation of immunoglobulin light chain gene rearrangements during early B cell development in the human." *Eur. J. Immunol.* 31: 3631-37 (2001).
8. Breger, K. S., Smith, L., Thayer. M. J. "Engineering translocations with delayed replication: Evidence for cis control of chromosome replication timing." *Hum. Mol. Genet.* 14: 2813-27 (2005).
9. Chang, B. H., Smith, L., Huang, J., Thayer, M. "Chromosomes with delayed replication timing lead to checkpoint activation, delayed recruitment of Aurora B and chromosome instability." *Oncogene* 26: 1852-61 (2007).
10. Chen, Y., Deng, J., Fujimoto, J., Kadara, H., Men, T., Lotan, D., Lotan, R. "Gprc5a deletion enhances the transformed phenotype in normal and malignant lung epithelial cells by eliciting persistent Stat3 signaling induced by autocrine leukemia inhibitory factor." *Cancer Res.* 70: 8917-26 (2010).
11. Collins-Underwood, J. R., Mullighan, C. G. "Genomic profiling of high-risk acute lymphoblastic leukemia." *Leukemia* 24: 1676-85 (2010).
12. Compte E, Pontarotti P, Collette Y, Lopez M, Olive D. 2004. Frontline: Characterization of BT3 molecules belonging to the B7 family expressed on immune cells. *Eur. J. Immunol.* 34: 2089-99 (2004).
13. Coolen, M. W., Stirzaker, C., Song, J. Z., Statham, A. L., Kassir, Z., Moreno C. S., Young, A. N., Varma, V., Speed, T. P., Cowley, M., et al. "Consolidation of the cancer genome into domains of repressive chromatin by long-range epigenetic silencing (LRES) reduces transcriptional plasticity." *Nat. Cell. Biol.* 12: 235-46 (2010).
14. Dallosso, A. R., Oster, B., Greenhough, A., Thorsen, K., Curry, T. J., Owen, C., Hancock, A. L., Szemes, M., Paraskeva, C., Frank, M., et al. "Long-range epigenetic silencing of chromosome 5q31 protoc adherins is involved in early and late stages of colorectal tumorigenesis through modulation of oncogenic pathways." *Oncogene doi:* 10.1038/onc.2011.609 (2012).
15. De. S., Michor, F. "DNA replication timing and long-range DNA interactions predict mutational landscapes of cancer genomes." *Nat. Biotechnol.* 29: 1103-08 (2011).
16. Eul, J., Gronemeyer, H., Adolph, S., Hameister, H. "Suppression of tumorigenicity in T-cell lymphoma hybrids is correlated with changes in myc expression and DNA replication of the myc chromosomal domain." *Chromosoma* 96: 248-54 (1988).
17. Ferrando, A. A., Neuberg, D. S., Staunton, J., Loh, M. L., Huard, C., Raimondi, S. C., Behm, F. G., Pui, C. H., Downing, J. R., Gilliland, D. G., et al. "Gene expression signatures define novel oncogenic pathways in T cell acute lymphoblastic leukemia." *Cancer Cell* 1: 75-87 (2002).
18. Gilbert, D. M. "Evaluating genome-scale approaches to eukaryotic DNA replication." *Nat. Rev. Genet.* 11: 673-84 (2010).
19. Hansen, K. D., Timp, W., Bravo, H. C., Sabunciyan, S., Langmead, B., McDonald, O. G., Wen, B., Wu, H., Liu, Y., Diep, D., et al. "Increased methylation variation in epigenetic domains across cancer types." *Nat. Genet.* 43: 768-75 (2011).
20. Hiraoka, N., Nakagawa, H., Ong, E., Akama, T. O., Fukuda, M. N., Fukuda, M. "Molecular cloning and expression of two distinct human chondroitin 4-O-sulfotransferases that belong to the HNK-1 sulfotransferase gene family." *J. Biol. Chem.* 275: 20188-96 (2000).
21. Hiratani, I., Ryba, T., Itoh, M., Yokochi, T., Schwaiger, M., Chang, C. W., Lyou, Y., Townes, T. M., Schubeler, D., Gilbert, D. M. "Global reorganization of replication 22. Hiratani, I., Takebayashi, S., Lu, J., Gilbert, D. M. "Replication timing and transcriptional control: Beyond cause and effect—part II." *Curr. Opin. Genet. Dev.* 19: 142-49 (2009).
23. Hiratani, I., Ryba, T., Itoh, M., Rathjen, J., Kulik, M., Papp, B., Fussner, E., Bazett-Jones, D. P., Plath, K., Dalton, S., et al. "Genome-wide dynamics of replication timing revealed by in vitro models of mouse embryogenesis." *Genome Res.* 20: 155-69 (2010).
24. Horsley, S. W., Mackay, A., Iravani, M., Fenwick, K., Valgeirsson, H., Dexter, T., Ashworth, A., Kearney, L. "Array CGH of fusion gene-positive leukemia-derived cell lines reveals cryptic regions of genomic gain and loss." *Genes Chromosomes Cancer* 45: 554-64 (2006).
25. Hsu, P. Y., Hsu, H. K., Singer, G. A., Yan, P. S., Rodriguez, B. A., Liu, J. C., Weng, Y. I., Deatherage, D. E., Chen, Z., Pereira, J. S., et al. Estrogen-mediated epigenetic repression of large chromosomal regions through DNA looping. *Genome Res.* 20: 733-44 (2010).
26. Hunger, S. P., Fall, M. Z., Camitta, B. M., Carroll, A. J., Link, M. P., Lauer, S. J., Mahoney, D. H., Pullen, D. J., Shuster, J. J., Steuber, C. P., et al. "E2A-PBX1 chimeric transcript status at end of consolidation is not predictive of treatment outcome in childhood acute lymphoblastic leukemias with a t(1;19)(q23;p13): A Pediatric Oncology Group study." *Blood* 91: 1021-28 (1998).
27. Jeha, S., Pui, C. H. "Risk-adapted treatment of pediatric acute lymphoblastic leukemia." *Hematol. Oncol. Clin. North Am.* 23: 973-90 (2009).
28. Kearney, L., Horsley, S. W. "Molecular cytogenetics in haematological malignancy: current technology and future prospects." *Chromosoma* 114: 286-94 (2005).
29. Korenstein-Ilan, A., Amiel, A., Lalezari, S., Lishner, M., Avivi, L. "Allele-specific replication associated with aneuploidy in blood cells of patients with hematologic malignancies." *Cancer Genet. Cytogenet.* 139: 97-103 (2002).
30. Lieberman-Aiden, E, van Berkum, N. L., Williams, L., Imakaev, M., Ragoczy, T., Telling, A., Amit, I., Lajoie, B. R., Sabo, P. J., Dorschner, M. O., et al. "Comprehensive mapping of long-range interactions reveals folding principles of the human genome." *Science* 326: 289-93 (2009).
31. Liu, P., Erez, A., Nagamani, S. C., Dhar, S. U., Kolodziejska, K. E., Dharmadhikari, A. V., Cooper, M. L., Wiszniewska, J., Zhang, F., Withers, M. A., et al. "Chromosome catastrophes involve replication mechanisms generating complex genomic rearrangements." *Cell* 146: 889-903 (2011).
32. Luo, X. Q., Ke, Z. Y., Huang, L. B., Guan, X. Q., Zhang, Y. C., Zhang, X. L. "High-risk childhood acute lymphoblastic leukemia in China: Factors influencing the treatment and outcome." *Pediatr. Blood Cancer* 52: 191-95 (2009).
33. Marcucci, G., Baldus, C. D., Ruppert, A. S., Radmacher, M. D., Mrozek, K., Whitman, S. P., Kolitz, J., Edwards, C. G., Vardiman, J. W., Powell, B. L., et al. "Over expression of the ETS-related gene, ERG, predicts a worse outcome in acute myeloid leukemia with normal karyotype: A cancer and leukemia group B study." *J. Clin. Oncol.* 23: 9234-42 (2005).
34. Mathas, S., Kreher, S., Meaburn, K. J., Johrens, K., Lamprecht, B., Assaf, C., Sterry, W., Kadin, M. E., Daibata, M., Joos, S., et al. "Gene deregulation and spatial genome reorganization near breakpoints prior to formation of translocations in anaplastic large cell lymphoma." *Proc. Natl. Acad. Sci.* 106: 5831-36 (2009).
35. McKenna, R. W., Washington, L. T., Aquino, D. B., Picker, L. J., Kroft, S. H. "Immunophenotypic analysis of hematogones (B-lymphocyte precursors) in 662 consecutive bone marrow specimens by 4-color flow cytometry." *Blood* 98: 2498-2507 (2001).
36. Mullighan, C. G., Goorha, S., Radtke, I., Miller, C. B., Coustan-Smith, E., Dalton, J. D., Girtman, K., Mathew, S., Ma, J., Pounds, S. B., et al. "Genome-wide analysis of genetic alterations in acute lymphoblastic leukaemia." *Nature* 446: 758-764.
37. Nemazee, D. "Receptor editing in lymphocyte development and central tolerance." *Nat. Rev. Immunol.* 6: 728-40 (2006).
38. Niebuhr, B., Fischer, M., Tager, M., Cammenga, J., Stocking, C. "Gatekeeper function of the RUNX1 transcription factor in acute leukemia." *Blood Cells Mol. Dis.* 40: 211-18 (2008).
39. Okuda, T., Mita, S., Yamauchi, S., Matsubara, T., Yagi, F., Yamamori, D., Fukuta, M., Kuroiwa, A., Matsuda, Y., Habuchi, O. "Molecular cloning, expression, and chromosomal mapping of human chondroitin 4-sulfotransferase, whose expression pattern in human tissues is different from that of chondroitin 6-sulfotransferase." *J. Biochem.* 128: 763-70. (2000).
40. Pope, B. D., Tsumagari, K., Battaglia, D., Ryba, T., Hiratani, I., Ehrlich, M., Gilbert, D. M. "DNA replication timing is maintained genome-wide in primary human myoblasts independent of D4Z4 contraction in FSH muscular dystrophy." *PLoS ONE* 6: e27413. doi: 10.1371/journal.pone.0027413 (2011).
41. Pui, C. H., Carroll, W. L., Meshinchi, S., Arceci, R. J. "Biology, risk stratification, and therapy of pediatric acute leukemias: An update." *J. Clin. Oncol.* 29: 551-65 (2011).
42. Pujadas, E., Feinberg, A. P. "Regulated noise in the epigenetic landscape of development and disease." *Cell* 148: 1123-31 (2012).
43. Rhodes, D. A., Stammers, M., Malcherek, G., Beck, S., Trowsdale, J. "The cluster of BTN genes in the extended major histocompatibility complex." *Genomics* 71: 351-62 (2001).
44. Ryba, T., Hiratani, I., Lu, J., Itoh, M., Kulik, M., Zhang, J., Schulz, T. C., Robins, A. J., Dalton, S., Gilbert, D. M. "Evolutionarily conserved replication timing profiles predict long-range chromatin interactions and distinguish closely related cell types." *Genome Res.* 20: 761-70 (2010).
45. Ryba, T., Battaglia, D., Pope, B. D., Hiratani, I., Gilbert, D. M. "Genome-scale analysis of replication timing: From bench to bioinformatics." *Nat. Protoc.* 6: 870-95 (2011a).
46. Ryba, T., Hiratani, I., Sasaki, T., Battaglia, D, Kulik, M., Zhang, J., Dalton, S., Gilbert, D. M. "Replication timing: A fingerprint for cell identity and pluripotency." *PloS Comput. Biol.* 7: e1002225.doi: 10.1371/journal.pcbi.1002225 (2011b).
47. Schlesinger, S., Selig, S., Bergman, Y., Cedar, H. "Allelic inactivation of rDNA loci." *Genes Dev.* 23: 2437-47 (2009).
48. Schmidt, H. H., Dyomin, V. G., Palanisamy, N., Itoyama, T., Nanjangud, G., Pirc-Danoewinata, H., Haas, O. A., Chaganti, R. S. "Deregulation of the carbohydrate (chondroitin 4) sulfotransferase 11 (CHST11) gene in a B-cell chronic lymphocytic leukemia with a t(12;14)(q23;q32)." *Oncogene* 23: 6991-96 (2004).

49. Smith, L., Plug, A., Thayer, M. "Delayed replication timing leads to delayed mitotic chromosome condensation and chromosomal instability of chromosome translocations." *Proc. Natl. Acad. Sci.* 98: 13300-05 (2001).
50. Smith, I. A., Knezevic, B. R., Ammann, J. U., Rhodes, D. A., Aw, D., Palmer, D. B., Mather, I. H., Trowsdale, J. "BTN1A1, the mammary gland butyrophilin, and BTN2A2 are both inhibitors of T cell activation." *J. Immunol.* 184: 3514-25 (2010).
51. Strefford, J. C., An, Q., Harrison, C. J. "Modeling the molecular consequences of unbalanced translocations in cancer: Lessons from acute lymphoblastic leukemia." *Cell Cycle* 8: 2175-84 (2009).
52. Sun, Y., Wyatt, R. T., Bigley, A., Krontiris, T. G. "Expression and replication timing patterns of wildtype and translocated BCL2 genes." *Genomics* 73: 161-70 (2001).
53. Tang, J. Q., Bene, M. C., Faure, G. C. "Alternative rearrangements of immunoglobulin light chain genes in human leukemia." *Leukemia* 5: 651-656 (1991).
54. Tao, Q., Fujimoto, J., Men, T., Ye, X., Deng, J., Lacroix, L., Clifford, J. L., Mao, L., Van Pelt, C. S., Lee. J. J., et al. "Identification of the retinoic acid-inducible Gprc5a as a new lung tumor suppressor gene." *J. Natl. Cancer. Inst.* 99: 1668-82 (2007).
55. Usvasalo, A., Raty, R., Harila-Saari, A., Koistinen, P., Savolainen, E. R., Vettenranta, K., Knuutila, S., Elonen, E., Saarinen-Pihkala, U. M. "Acute lymphoblastic leukemias with normal karyotypes are not without genomic aberrations." *Cancer Genet. Cytogenet.* 192: 10-17 (2009).
56. Weddington, N., Stuy, A, Hiratani, I., Ryba, T., Yokochi, T., Gilbert, D. M., "Replication Domain: A visualization tool and comparative database for genome-wide replication timing data." *BMC Bioinformatics* 9: 530. doi: 10.1186/1471-2105-9-330 (2008).
57. Wiemels, J. L., Alexander, F. E., Cazzaniga, G., Biondi, A., Mayer, S. P., Greaves, M., "Microclustering of TEL-AML1 translocation breakpoints in childhood acute lymphoblastic leukemia." *Genes Chromosomes Cancer* 29: 219-28 (2000).
58. Xu, J., Sankaran, V. G., Ni, M., Menne, T. F., Puram, R. V., Kim, W., Orkin S. H. "Transcriptional silencing of g-globin by BCL11A involves long-range interactions and cooperation with SOX6." *Genes Dev.* 24: 783-98 (2010).
59. Yeoh, E. J., Ross, M. E., Shurtleff, S. A., Williams, W. K., Patel, D., Mahfouz, R., Behm, F. G., Raimondi, S. C., Relling, M. V., Patel, A., et al. "Classification, subtype discovery, and prediction of outcome in pediatric acute lymphoblastic leukemia by gene expression profiling." *Cancer Cell* 1: 133-43 (2002).
60. Ryba, T., Battaglia, D., Chang, B. H., Shirley, J. W., Buckley, Q., Pope, B. D., Devidas, M., Druker, B. J., and Gilbert D. M. "Abnormal developmental control of replication-timing domains in pediatric acute lymphoblastic leukemia," *Genome Res.* 22(10):1833-44 (2012),

What is claimed is:
1. A method comprising the following steps:
    (a) generating a loess-smoothed replication timing profile for a population of cells,
    (b) comparing the loess-smoothed replication timing profile for the population of cells to loess-smoothed replication timing reference profiles for a plurality of different leukemic cell types, which are contained in a database,
    (c) based on the comparison of step (b), identifying the population of cells as having a leukemic cell type that is one of the plurality of different leukemic cell types if the loess-smoothed replication timing profile is determined to be substantially the same as the loess-smoothed replication timing reference profile for the leukemic cell type, and
    (d) displaying the cell type identified in step (c) to a user, wherein steps (a), (b), (c) and (d) are performed by a computer configured to perform steps (a), (b), (c) and (d).
2. The method of claim 1, wherein the population of cells is identified as being a population of chronic or acute leukemia cells in step (c).
3. The method of claim 1, wherein the population of cells is identified as being a population of chronic lymphocytic leukemia (CLL) cells in step (c).
4. The method of claim 1, wherein the population of cells is identified as being a population of chronic myeloid leukemia (CML) cells in step (c).
5. The method of claim 1, wherein the population of cells is identified as being a population of acute lymphocytic (lymphoblastic) leukemia (ALL) cells in step (c).
6. The method of claim 1, wherein the population of cells is identified as being a population of acute myeloid leukemia (AML) cells in step (c).
7. A computer comprising a program for performing the following steps:
    (a) generating a loess-smoothed replication timing profile for a population of cells,
    (b) comparing the loess-smoothed replication timing profile for the population of cells to loess-smoothed replication timing reference profiles for a plurality of different leukemic cell types, which are contained in a database,
    (c) based on the comparison of step (b), identifying the population of cells as having a leukemic cell type that is one of the plurality of different leukemic cell types if the loess-smoothed replication timing profile is determined to be substantially the same as the loess-smoothed replication timing reference profile for the leukemic cell type, and
    (d) displaying the cell type identified in step (c) to a user.

* * * * *